US012710426B2

(12) United States Patent
Berghmans et al.

(10) Patent No.: US 12,710,426 B2
(45) Date of Patent: Aug. 18, 2026

(54) IMMUNOTHERAPY MARKERS

(71) Applicants: VITO NV, Mol (BE); UNIVERSITEIT ANTWERPEN, Antwerp (BE)

(72) Inventors: Eline Berghmans, Mol (BE); Geert Baggerman, Mol (BE); Evelien Smits, Antwerp (BE); Patrick Pauwels, Prinsstraat (BE)

(73) Assignees: VITO NV, Mol (BE); Universiteit Antwerpen, Antwerp (BE)

( * ) Notice: Subject to any disclaimer, the term of this patent is extended or adjusted under 35 U.S.C. 154(b) by 1191 days.

(21) Appl. No.: 17/760,673

(22) PCT Filed: Sep. 14, 2020

(86) PCT No.: PCT/EP2020/075666

§ 371 (c)(1),
(2) Date: Mar. 15, 2022

(87) PCT Pub. No.: WO2021/052915

PCT Pub. Date: Mar. 25, 2021

(65) Prior Publication Data

US 2023/0051633 A1 Feb. 16, 2023

(30) Foreign Application Priority Data

Sep. 16, 2019 (EP) .................................... 19197602

(51) Int. Cl.
*G01N 33/575* (2026.01)
*G01N 33/68* (2006.01)

(52) U.S. Cl.
CPC ..... *G01N 33/5758* (2026.01); *G01N 33/6851* (2013.01); *G01N 2333/4721* (2013.01); *G01N 2800/52* (2013.01)

(58) Field of Classification Search
CPC ..... G01N 33/57484; G01N 2333/4721; G01N 2800/52
See application file for complete search history.

(56) References Cited

FOREIGN PATENT DOCUMENTS

| | | | |
|---|---|---|---|
| EP | 2484762 | A1 | 8/2012 |
| EP | 2589665 | A1 | 5/2013 |
| WO | 2016183326 | A1 | 11/2016 |

OTHER PUBLICATIONS

Droin et al., Journal of Proteomics, 72: 918-927 (Year: 2009).*
Wehder et al. J Histochem Cytochem. Oct. 2010;58(10):929-37. (Year: 2010).*
Xu D, Lu W. Defensins: A Double-Edged Sword in Host Immunity. Front Immunol. May 7, 2020;11:764. (Year: 2020).*
Boldt, Clayton. MD Anderson Cancer Center, "Why doesn't immunotherapy work for everyone?" Sep. 30, 2020. (Year: 2020).*
Joshua A. Bauer et al., Identification of markers of taxane sensitivity using proteomic and genomic analyses of breast tumors from patients receiving neoadjuvant paclitaxel and radiation. Clin. Cancer Res. 2010, 16, 681-690.
Edward B. Garon et al., Pembrolizumab for the Treatment of Non-Small-Cell Lung Cancer, The New England Journal of Medicine, 2015, 372, 2018-2028.
Cecilia Zappa et al., Non-small cell lung cancer: current treatment and future advances, Translational Lung Cancer Research, Jun. 2016, vol. 5, No. 3.
Pankaj Kumar Singh et al., Kinases inhibitors in lung cancer: From benchside to bedside, Biochim. Biophys. Acta Rev. Cancer 2016, 1866, 128-140.
Drew M. Pardoll, The blockade of immune checkpoints in cancer immunotherapy, Nat. Rev. Cancer 2012, 12, 252-264.
Douglas B. Johnson et al., Nivolumab in melanoma: latest evidence and clinical potential, Ther Adv Med Oncol, 2015, 7, 97-106.
Claudia A. Muller et al., Human-Defensins HNPs-1, -2, and -3 in Renal Cell Carcinoma, Am. J. Pathol. 2002, 160, 1311-1324.
J.L. Riley, PD-1 signaling in primary T cells, Immunol Rev. 2009, 229, 114-125.
I. Mellman et al., G. Cancer immunotherapy comes of age, Nature 2014, 480, 480-489.
Zhenqing Ye et al., Prevalent Homozygous Deletions of Type I Interferon and Defensin Genes in Human Cancers Associate with Immunotherapy Resistance, Clin. Cancer Res. 2018.
Bernard Metz et al., Identification of Formaldehyde-Induced Modifications in Proteins: Reactions with Insulin, Bioconjugate Chem. 2006, 17, 815-822.
Marianne Davies, New modalities of cancer treatment for NSCLC: focus on immunotherapy, Cancer Manag. Res. 2014, 6, 63-7 5.
F. Rahimi et al., Antigen-Epitope Retrieval to Facilitate Proteomic Analysis of Formalin-Fixed Archival Brain Tissue, Anal. Chem. 2006, 78, 7216-7221.
Hannah A. Blair, Atezolizumab: A Review in Previously Treated Advanced Non-Small Cell Lung Cancer, Target. Oncol. 2018, 13, 399-407.
Nancy Tray et al., Predictive Biomarkers for Checkpoint Immunotherapy: Current Status and Challenges for Clinical Application, Cancer Immunol. Res. 2018, 6, 1122-1128.
Ricardo E. Vilain et al., Dynamic changes in PD-L1 expression and immune infiltrates early during treatment predict response to PD-1 blockade in melanoma, Clin. Cancer Res. 2017, 23, 5024-5033.
Monica Khunger et al., Programmed Cell Death 1 (PD-1) Ligand (PD-L1) Expression in Solid Tumors as a Predictive Biomarker of Benefit From PD-1/PD-L1 Axis Inhibitors: A Systematic Review and Meta-Analysis, JCO Precis. Oncol. 2017, 1, 1-15.

(Continued)

*Primary Examiner* — Jeffrey Stucker
*Assistant Examiner* — Sarah Cooper Patterson
(74) *Attorney, Agent, or Firm* — DINSMORE & SHOHL LLP

(57) ABSTRACT

The present invention relates to the identification and use of markers indicative for the response of a subject to immunotherapy as anti-cancer treatment. The markers are particularly useful in predicting response of a subject to immunotherapy with PD-1 or PD-L1 antagonists in the treatment of cancer. PD-1 and PD-L1 antagonists are typically used as immunotherapy in the treatment of several types of cancer, including melanoma, non-small cell lung cancer (NSCLC), and squamous cell carcinoma.

12 Claims, 13 Drawing Sheets

Specification includes a Sequence Listing.

(56) References Cited

OTHER PUBLICATIONS

Vamsidhar Velcheti et al., Programmed death ligand-1 expression in non-small cell lung cancer, Lab Invest 2014, 94, 107-116.
Caroline Robert et al., Nivolumab in Previously Untreated Melanoma without BRAF Mutation, N. Engl. J. Med. 2015, 372, 320-330.
Adil I. Daud et al., Programmed Death-Ligand 1 Expression and Response to the Anti-Programmed Death 1 Antibody Pembrolizumab in Melanoma, J. Clin. Oncol. 2016, 34, 4102-4109.
Janis M. Taube et al., Association of PD-1, PD-1 Ligands, and Other Features of the Tumor Immune Microenvironment with Response to Anti-PD-1 Therapy, Clin Cancer Res 2015, 20, 5064-5074.
Julie Jacobs et al., Unlocking the potential of CD70 as a novel immunotherapeutic target for non-small cell lung cancer, Oncotarget 2015, 6, 13462-13475.
C. Teixido et al., Assays for predicting and monitoring responses to lung cancer immunotherapy, Cancer Biol. Med. 2015, 12, 87-95.
Eline Berghmans et al., Mass Spectrometry Imaging Reveals Neutrophil Defensins as Additional Biomarkers for Anti-PD-(L)1 Immunotherapy Response in NSCLC Patients, Cancers 2020, 12, 863, 1-22.
Kamila Chughtai et al., Mass Spectrometric Imaging for Biomedical Tissue Analysis, Chem. Rev. 2010, 110, 3237-3277.
Dorothy R. Ahlf Wheatcraft et al., Sample Preparation Strategies for Mass Spectrometry Imaging of 3D Cell Culture Models, J. Vis. Exp. 2014, 1-7.
Laurens Minerva et al., Direct profiling and identification of peptide expression differences in the pancreas of control and ob/ob mice by imaging mass spectrometry, Proteomics 2008, 8, 3763-3774.
Markus Stoeckli et al., Imaging mass spectrometry: A new technology for the analysis of protein expression in mammalian tissues, Nat. Med. 2001, 7, 493-496.
L. Minerva et al., Linking Mass Spectrometric Imaging and Traditional Peptidomics: A Validation in the Obese Mouse Model, Anal. Chem. 2011, 83, 7682-7691.
Ling-Juan Zhang et al., Antimicrobial peptides, Curr. Biol. 2016, 26, 14-19.
Jennifer K. Plichta et al., Integrating "omics" technologies to conceptualize dynamic antimicrobial peptide responses, Front. Immunol. 2012, 3, 1-4.
Tomas Ganz, The Role of Antimicrobial Peptides in Innate Immunity, Integr. Comp. Biol. 2003, 43, 300-304.
H. Mukae et al., S. Raised plasma concentrations of a-defensins in patients with idiopathic pulmonary fibrosis, Thorax 2002, 57, 623-628.
A. Stenzinger et al., Combined Immunohistochemistry after Mass Spectrometry Imaging for superior spatial information, PROTEOMICS—Clin. Appl. 2018, 13, 1800035.
Melanie Christine Foll et al., Reproducible proteomics sample preparation for single FFPE tissue slices using acid-labile surfactant and direct trypsinization, Clin. Proteomics 2018, 15, 1.
Kyle D. Bemis et al., Cardinal: an R package for statistical analysis of mass spectrometry-based imaging experiments, Bioinformatics 2015, 31, 2418-2420.
Ryan T. Fellers et al., ProSight Lite: Graphical Software to Analyze Top Down Mass Spectrometry Data, Proteomics 2015, 15, 1235-1238.
Rita Casadonte et al., Proteomic analysis of formalin-fixed paraffin-embedded tissue by MALDI imaging mass spectrometry, Nat. Protoc. 2012, 6, 1695-1709.
A. Ly et al., High-mass-resolution MALDI mass spectrometry imaging of metabolites from formalin-fixed paraffin- embedded tissue, Nat. Protoc. 2016, 11, 1428-1443.
Scott R. Cole et al., Electron Transfer Dissociation (ETD) of Peptides Containing Intrachain Disulfide Bonds, J. Am. Soc. Mass Spectrom. 2012, 23, 310-320.
Shiaw-Lin Wu et al., Mass Spectrometric Determination of Disulfide Linkages in Recombinant Therapeutic Proteins Using On-line LC-MS with Electron Transfer Dissociation (ETD), Anal. Chem. 2009, 81, 112-122.
Philip D. Compton et al., Optimization of Electron Transfer Dissociation via Informed Selection of Reagents and Operating Parameters, Anal. Chem. 2012, 84, 1781-1785.
Diana Gaspar et al., Apoptotic human neutrophil peptide-1 anti-tumor activity revealed by cellular biomechanics, Biophys. Acta—Mol. Cell Res. 2015, 1853, 308-316.
Ning Xu et al., Human-defensin-1 inhibits growth of human lung adenocarcinoma xenograft in nude mice, Mol. Cancer Ther. 2008, 7, 1588-1597.
Andrew Bateman et al., The Levels and Biologic Action of the Human Neutrophil Granule Peptide HP-1 in Lung Tumors, Peptides 1992, 13, 133-139.
International Search Report and Written opinion dated Dec. 3, 2020 pertaining to PCT Application No. PCT/EP2020/075666 filed Sep. 14, 2020.
Extended European Search Report dated Mar. 20, 2020 pertaining to EP Application No. 19197602.6 filed Sep. 16, 2019.
Gabriel Etienne: [alpha]-Defensin 1-3 and [alpha]-Defensin 4 as Predictive Markers of Imatinib Resistance and Relapse in CML Patients, Disease markers, vol. 30; Jan. 1, 2011 (Jan. 1, 2011), pp. 221-227 XP055674687, United States, DOI: 10.3233/DMA-2011-0777; Retrieved from the Internet: URL: https://www.hindawi.com/journals/dm/2011/287690.
J. A. Bauer et al: Identification of Markers of Taxane Senseitivity Using Proteomic and Genomic Analysis of Breast Tumors from Patients Receiving Neoadjuvant Paclitaxel and Radiation, Clinical Cancer Research, vol. 16, No. 2, Jan. 15, 2010 (Jan. 15, 2010) , pp. 681-690, XP055073331, ISSN: 1078-0432, DOI: 10.1158/1078-0432. CCR-09-1091.
Eline Berghmans et al. Mass Spectrometry Imaging Reveals Neutrophil Defensins as Additional Biomarkers for Anti-PD-(L)I Immunotherapy Response in NSCLC Patients, CANCERS, vol. 12, No. 4, Apr. 2, 2020 (Apr. 2, 2020), p. 863, XP055753611, D01: 10.3390/cancers12040863.

* cited by examiner

Responders

IMMUNOTHERAPY MARKERS

CROSS-REFERENCES TO RELATED APPLICATIONS

This application is a national-stage application under 35 U.S.C. § 371 of International Application No. PCT/EP2020/075666, filed Sep. 14, 2020, which International Application claims benefit of priority to European Patent Application No. 19197602.6, filed Sep. 16, 2019.

SEQUENCE LISTING

A computer-readable form (CRF) sequence listing having file name VTV0001PASEQLISTING.txt (2 kb), created on Mar. 7, 2022, is incorporated herein by reference. The amino acid sequences listed in the accompanying sequence listing are shown using standard abbreviations as defined in 37 C.F.R. § 1.822.

FIELD OF THE INVENTION

The present invention relates to the identification and use of markers indicative for the response of a subject to immunotherapy as anti-cancer treatment. The markers are particularly useful in predicting response of a subject to immunotherapy with PD-1 or PD-L1 antagonists in the treatment of cancer. PD-1 and PD-L1 antagonists are typically used as immunotherapy in the treatment of several types of cancer, including melanoma, non-small cell lung cancer (NSCLC), and squamous cell carcinoma.

BACKGROUND TO THE INVENTION

Advanced non-small-cell lung cancer (NSCLC), accounting for 85% of all lung cancer cases, is generally linked with a poor prognosis and is one of the leading causes of cancer-related deaths worldwide for both women and men [1]. Since only a minority of these NSCLC patients respond well to chemotherapy and/or targeted therapies, immunotherapy might be a valid alternative in the lung cancer treatment field [2].

Adenocarcinoma is the most common NSCLC type and the slower growing type compared to the others, with a higher chance to be found before spreading outside the lungs. It arises from early epithelial cells responsible for mucus secretion [3]. The second type, squamous cell carcinoma, emerges from flat cells lining the inside of bronchial tubes [3]. The smallest amount of NSCLC patients are diagnosed with large cell (undifferentiated) carcinoma and tends to grow and spread more quickly, with a higher risk to evolve to distant organs [3]. These subtypes can start from different types of cells in the lung, but the approaches to (immunotherapy) treatment and prognosis are often similar [4].

The most promising approach of immunotherapy is the therapeutic blocking of immune checkpoints to restore the anti-tumor immune response [5]. Immune checkpoints are regulatory cell surface molecules to end ineffective immune responses and maintain self-tolerance [6]. It has been established that many tumor cells show immune resistance by expression of such cell surface molecules to modulate T cell activation and prevent in this way T cell immune activation to recognize and destroy the tumor cells [5], [6]. The first immunotherapy agent to demonstrate an improvement in overall survival was Ipilimumab, a monoclonal antibody that inhibits cytotoxic T-lymphocyte antigen 4 (CTLA-4) interaction with antigen presenting cells (APC), which resulted in antitumor response in some patients [6]. Due to severe toxicities caused by Ipilimumab, such as immune-related adverse events, substantial morbidity and even mortality [6], therapy with Ipilimumab is rarely used for NSCLC treatment, but appears in combinatorial approaches with the therapies listed further [5]. One of the most exciting immunotherapies, and of our focus for this study, includes the reactivation of immune T cell mediated anti-tumor activity by inhibiting the PD-1/PD-L1 interaction [7]. Programmed death-1 (PD-1) is a T cell surface molecule that interacts with its ligand PD-L1 to downregulate T cell activation [8]. However, NSCLC tumor cells can escape immune destruction by expression of PD-L1 through binding to the regulatory T cell receptor PD-1, that causes T cell exhaustion [7], [9]. These T cell responses can be recovered by therapeutic blockade of the PD-1/PD-L1 interaction; immunotherapy treatments Pembrolizumab [10] and Nivolumab [11], both antagonists of the immune checkpoint PD-1, have demonstrated improved clinical outcomes, in terms of acceptable side-effects and anti-tumor activity by restoring host immunity [2], [7], [12]. Atezolizumab [13] immunotherapy treatment, an antagonist of the immune checkpoint ligand PD-L1, also showed promising results in the lung cancer treatment field [14]. Much uncertainty still exists about unique response patterns of these immunotherapies and the majority of NSCLC patients are selected for immunotherapy treatment without deriving any benefit and in addition showing severe side-effects [12], [15]. This is due to limitations of PD-L1 protein expression as currently sole predictive biomarker in clinical use [7], [16]; although different studies suggest high PD-L1 expression pivotal for successful cancer immunotherapy [2], [17], [18], patients with low to no PD-L1 expression can also derive benefit [19], [20] and moreover, not every patient with obvious PD-L1 expression demonstrates a positive clinical response to the immunotherapy treatments [21]. There is thus a high need to evaluate other factors within the tumor microenvironment associated with clinical benefit to immunotherapy, specifically focused on therapeutic blockade of the PD-1/PD-L1 interaction [21]-[23]. The aim of this study is establishing additional biomarkers of response for immunotherapy treatment, to obtain long-lasting responses in NSCLC patients and to avoid immunotherapy treatment of NSCLC patients who clinically do not respond.

SUMMARY OF THE INVENTION

We have demonstrated earlier that MALDI mass spectrometry imaging (MSI) has been recognized as a powerful tool to better understand the lung tumor microenvironment, in terms of small immune-related factors [24]. MALDI mass spectrometry imaging is a multiplexed analysis and in theory provides the screening of all present molecules that can be ionized (i.e. broad variety of biomolecules as peptides, glycans, nucleic acids, lipids, metabolites, . . . ) directly from a single tissue section, without the need for target-specific reagents [25]-[27]. With MALDI MSI, a mass spectrum of each spot on the tissue is generated, which illustrates all the biomolecules present in that spot of the tissue, and all the individual recorded mass spectra are merged in one resulting overall average mass spectrum. The measurements are taken in a predefined order and this allows us to analyze both the distribution and relative abundances of each biomolecule over the entire tissue section [28]. MALDI MSI produces spatially resolved mass spectrometric data without destroying the tissue morphology, meaning that the same tissue slice can subsequently H&E stained after MALDI MSI analysis to combine both molecular and histological information [29]. Beside these advantages of MALDI $MS_1$, it is still cumbersome and often not possible to identify interesting MSI targets directly from the tissue itself. Therefore, we linked this technology with higher mass resolution mass spectrometry-based approaches, which made it feasible to reliably identify interesting small peptides/proteins, while retaining their spatial distribution throughout the lung tissue, required for a correct biological interpretation of the detected molecules within the area they are detected [24].

Since no prior knowledge of molecular identities is required for MSI experiments, crucial insights regarding antimicrobial peptide (AMP) profiles could be provided directly from lung cancerous tissues. AMPs, also referred to as 'host defense peptides', are naturally occurring molecules that comprises a major aspect of the host innate immune response [30], [31]. These are produced as a first line of defense to directly kill bacteria, yeast, etc. and more interesting for this study, also cancer cells [30] and may activate adaptive immunity [32]. Some AMPs are constitutively produced while the majority of AMPs are induced during infection, inflammation or injury [30], [32]. It has previously been observed that various molecular AMP signatures could be linked with human diseases, in terms of prognosis based upon a specific AMP profile, identification of predictive biomarkers and even determination of efficacy of various therapies [31], which is of major importance to predict the immunotherapy response in NSCLC patients. Therefore, we applied this newly developed MALDI MSI method to pre-treatment biopsies of NSCLC patients who received Pembrolizumab, Nivolumab or Atezolizumab as immunotherapy treatment. In this way, we have identified three antimicrobial peptides, i.e. neutrophil defensin 1, neutrophil defensin 2 and neutrophil defensin 3, which are associated with a positive immunotherapy response. Additionally, these proteomic findings were validated with immunohistochemical analyses, that can be used in clinical settings as pretreatment biomarker for prediction for immunotherapy response [33], [34]. Defensin 1-3 have previously been identified as markers in immunotherapy response, see for example Gabriel Etienne et al., Disease Markers, Vol. 30, 1 Jan. 2011; p. 221-227; EP2 484 762 or EP 2 589 665, but never as immunotherapy response markers in a treatment with a PD1 antagonist or a PD-L1 antagonist.

It is accordingly an objective of the present invention to provide methods and compositions that provide a companion diagnostic for immunotherapy, in particular for PD-1/PD-L1 antagonists, and for related methods of treating patients. In particular, the present invention relates to the use of one or more of the antimicrobial peptides selected from neutrophil defensin 1, neutrophil defensin 2 and neutrophil defensin 3, as biomarkers for evaluating whether a cancer can be successfully treated by immunotherapy, in particular for a treatment with PD-1/PD-L1 antagonists.

BRIEF DESCRIPTION OF THE DRAWINGS

FIG. 1C indicates the overall average mass spectrum of the whole tissue section obtained after MALDI MSI, which is zoomed out at the two peptides of interest m/z 3369.5 and m/z 3440.6 of which the corresponding distribution is displayed in FIGS. 1A and 1B. It shows that the peptides have a high expression in the nontumor region, a very high expression at the interaction border between the nontumor and tumor region and finally a very low until no expression further in the tumor region. These regions are confirmed with the H&E staining (FIG. 1B), performed on the same tissues section previously analyzed with MALDI MSI.

FIG. 2C indicates the overall average mass spectrum of the whole tissue section obtained after MALDI MSI, which is zoomed out at the three peptides of interest m/z 3369.5, m/z 3440.6 and m/z 3484.6 of which the corresponding distribution is displayed in FIGS. 2A-2B. It shows that the peptides are expressed in the nontumor region and in necrotic regions within the tumor region. These regions are confirmed in the corresponding H&E staining (FIG. 2B), performed after the MALDI MSI experiment on the same tissue section.

FIG. 3A. Full MS spectrum of intact neutrophil defensin 1, in three different charge states. The fifth charged ion with m/z 688.91 (mass 3439.55 Da as obtained with MSI in FIGS. 1, 2 and supplementary materials) is selected for reduction of the three cystein bridges with ETD and the reduced, intact peptide is immediately selected for fragmentation with CID. FIG. 3B. The resulting fragmentation spectrum with b, c, y and z type ions. FIG. 3C. Annotated sequence of Neutrophil defensin 1 with all matched deconvoluted fragments (see also table 1, mass accuracy was set at 300 ppm) obtained with both CID as ETD as fragmentation method.

FIG. 4A displays the distribution of each neutrophil defensin individually, after a MALDI MSI experiment.

FIG. 5A: average mass spectra of FFPE tissues from NSCLC patients with a positive response to immunotherapy. FIG. 5B: average mass spectra of FFPE tissues from NSCLC patients who received immunotherapy treatment but without clinical response to this therapy FIG. 6A: distribution of the three neutrophil defensins in FFPE lung tissue obtained after MALDI MSI. FIG. 6B includes a mass spectrum displaying the three neutrophil defensins, while the MSI image only displays the distribution of neutrophil defensin 1 (m/z 3440.6), as neutrophil defensin 1 shows the same distribution as neutrophil defensin 2 (m/z 3369.5) and 3 (m/z 3484.6). To validate the presence of the neutrophil defensins obtained with MALDI MSI, the region indicated with the box in FIG. 6A was compared with the same tissue region after immunohistochemical staining with defensin ⅓ antibody (upper image in FIG. 6B). This IHC result after MSI analysis was obtained after removal of the matrix with ethanol and antibody staining as described in materials and methods. When comparing the same IHC staining protocol on a consecutive FFPE tissue section with no prior MALDI MSI analysis (bottom right image in FIG. 6A), one can conclude that there is no change in staining intensity and that the visualized peptides in the MSI result were identified as neutrophil defensin 1, 2 and 3.

FIG. 7A: Full MS spectrum of intact neutrophil defensin 1, in three different charge states. The fifth charged ion with m/z 689.31 (mass 3441.6 Da) is selected for reduction of the three internal cystein bridges with ETD (activation time 200 ms). FIG. 7B: The resulting intact peptide m/z 1722.77 has lost three charges, one for each cystein bridge. This reduced peptide is immediately selected for fragmentation with CID (activation energy 45 for 70 ms). FIG. 7C: The resulting fragmentation spectrum with b, c, y and z type ions. FIG. 7D. Annotated sequence of Neutrophil defensin 1 with all matched deconvoluted fragments, obtained with both CID as ETD as fragmentation method.

FIG. 8A is an example of defensin ⅓ IHC negative case and FIG. 8B of defensin ⅓ IHC positive case. Magnification 40×.

DETAILED DESCRIPTION OF THE INVENTION

Figures 1A, 1B:
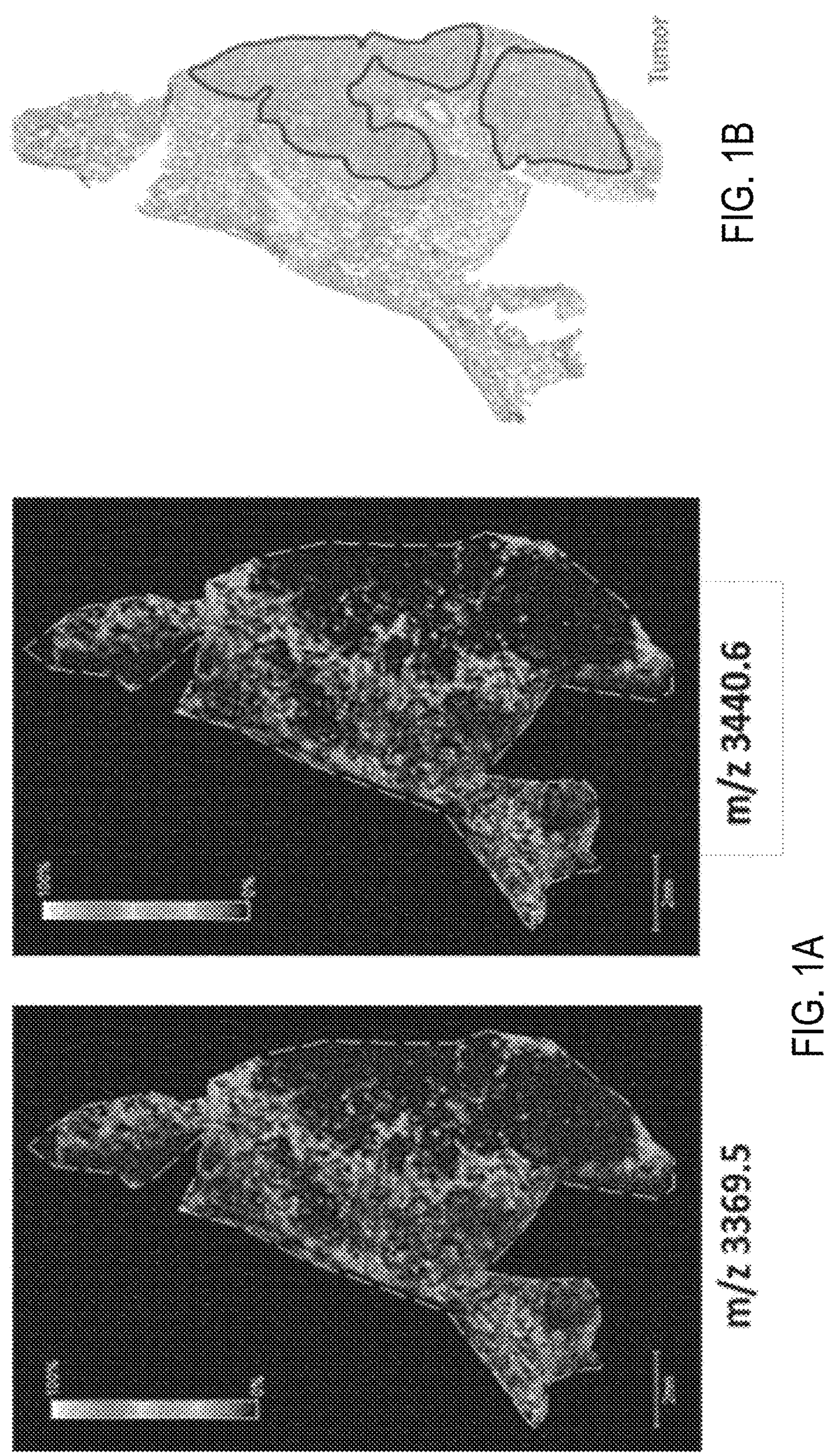
FIGS. 1A-1C: MALDI mass spectrometry imaging (MSI) showing the distribution of two peptides of interest m/z 3369.5 and m/z 3440.6 in human squamous cell carcinoma fresh frozen lung cancerous tissue (FIG. 1A) with adjacent H&E stained reference tissue (FIG. 1B).

As mentioned hereinbefore, the present invention, is based on the validation of the antimicrobial peptides selected from neutrophil defensin 1, neutrophil defensin 2 and neutrophil defensin 3 as biomarkers that can be used to determine if a cancer will be more likely to respond to immunotherapy; in particular to the treatment with a PD-1/PD-L1 antagonists.

Neutrophil Defensin 1

Neutrophil defensin 1 is also referred to as Defensin, Alpha, DEFA1, HNP-1 or HP-1. The present invention discloses Neutrophil defensin 1 as a biomarker.

The present invention discloses Neutrophil defensin 1 as a biomarker for cells that are more likely to respond immunotherapy; in particular to treatment with a PD-1/PD-L1 antagonist.

In a specific, non-limiting embodiment, Neutrophil defensin 1 may be detected using an immunodetection reagent specific for a Neutrophil defensin 1 protein for example but not by limitation, an antibody sold by Thermo Fisher, Goat-lgG Anti-Defensin ⅓ Polyclonal, Catalog #PA5-19228, an antibody sold by Abeam, Goat polyclonal alpha Defensin 1+2+3 antibody, Catalog #ab99504, or a fragment thereof.

In a specific, non-limiting embodiment, a Neutrophil defensin 1 protein may be a human Neutrophil defensin 1 protein having the amino acid precursor sequence as set forth in UniProt database accession no. P59665, and which is cleaved in a number of fragments including Neutrophil defensin 1, which is disclosed below as SEQ ID NO: 1; and Neutrophil Defensin 2 which is disclosed below as SEQ ID NO:2.

```
                                                      [SEQ ID NO: 1]
ACYCRIPACIAGERRYGTCIYQGRLWAFCC (Cystein bridges between Cys 1 and
Cys 6, between Cys 2 and Cys 4, between Cys 3 and Cys 5)

                                                      [SEQ ID NO: 2]
CYCRIPACIAGERRYGTCIYQGRLWAFCC (Cystein bridges between Cys 1 and
Cys 6, between Cys 2 and Cys 4, between Cys 3 and Cys 5)
```

Neutrophil Defensin 2

Neutrophil defensin 2 is also referred to as DEFA2, HNP-2 or HP-2. The present invention discloses Neutrophil defensin 2 as a biomarker.

The present invention discloses Neutrophil defensin 2 as a biomarker for cells that are more likely to respond immunotherapy; in particular to treatment with a PD-1/PD-L1 antagonist.

In a specific, non-limiting embodiment, Neutrophil defensin 2 may be detected using an immunodetection reagent specific for a Neutrophil defensin 2 protein for example but not by limitation, an antibody sold by Thermo Fisher, Goat-lgG Anti-Defensin ⅓ Polyclonal, Catalog #PA5-19228, an antibody sold by Abeam, Goat polyclonal alpha Defensin 1+2+3 antibody, Catalog #ab99504, or a fragment thereof.

Neutrophil Defensin 3 as a Biomarker

Neutrophil defensin 3 is also referred to as Defensin, Alpha 3, DEFA3, HNP-3 or HP-3. The present invention discloses Neutrophil defensin 3 as a biomarker. The present invention discloses Neutrophil defensin 3 as a biomarker for cells that are more likely to respond immunotherapy; in particular to treatment with a PD-1/PD-L1 antagonist.

In a specific, non-limiting embodiment, Neutrophil defensin 3 may be detected using an immunodetection reagent specific for a Neutrophil defensin 3 protein for example but not by limitation, an antibody sold by Thermo Fisher, Goat-lgG Anti-Defensin ⅓ Polyclonal, Catalog # PA5-19228, an antibody sold by Abeam, Goat polyclonal alpha Defensin 1+2+3 antibody, Catalog #ab99504, or a fragment thereof.

In a specific, non-limiting embodiment, a Neutrophil defensin 3 protein may be a human Neutrophil defensin 3 protein having the amino acid precursor sequence as set forth in UniProt database accession no. P59666, and which is cleaved in a number of fragments including Neutrophil defensin 3, which is disclosed below as SEQ ID NO: 3; and Neutrophil Defensin 2 which is disclosed as SEQ ID NO:2 above.

```
                                                      [SEQ ID NO: 3]
DCYCRIPACIAGERRYGTCIYQGRLWAFCC (Cystein bridges between Cys 1 and
Cys 6, between Cys 2 and Cys 4, between Cys 3 and Cys 5)
```

Methods of Detection

Methods for determining the localization of the protein biomarkers according to the invention, include, but are not limited to, immunofluorescence, immunoglobulin-mediated assays, Mass Spectrometry Imaging (MSI) and other techniques known in the art.

In certain, non-limiting embodiments, MSI, in particular MALDI-MSI can be used for detecting the antimicrobial peptides selected from neutrophil defensin 1, neutrophil defensin 2 and neutrophil defensin 3. MALDI-MSI uses the detection capability of mass spectrometry with the positional information of molecular histology, generating mass spectra correlated to known locations within a tissue. MALDI mass spectrometry imaging is able to reveal the distribution of a large range of analytes, including lipids, peptides and proteins directly from tissue sections. Preparation for MALDI requires a tissue section to be coated with a low molecular weight organic molecule, called the matrix. The most common matrix compounds used include but are not limited to 2,5-dihydroxybenoic acid (DHB), alpha-cyano-4-hydroxycinnamic acid (CHCA), and sinapinic acid (SA). Most matrixes are dissolved in a 50-60% acidified organic solvent solution, which extracts lipids, peptides and proteins from the tissue prior to evaporation, allowing the matrix to crystallize. The end result is a field of sample-matrix co-crystals on the tissue surface. MALDI is achieved by directing a laser beam at the co-crystals. The matrix absorbs the bulk of incident laser energy, causing an explosive transition from solid crystal to a gaseous plume, during which ionisation of the sample occurs. MALDI is suited to biomolecule analysis because it is a soft" ionisation process, in that the matrix is the energy absorber, minimizing protein/peptide fragmentation. MALDI ion sources are typically coupled to time-of-flight (TOF) mass analyzers. Ions from the MALDI process are accelerated into the TOF tube, which is an electric field free flight region. The kinetic energy gained during acceleration decreases with increasing mass and as such heavier ions will fly slower and therefore have a longer time-of-flight. This is the basis of TOF mass analysis. When an ion hits an attached detector, the time from laser ionisation to detection is used to derive m/z (see FIG. 1A). The end result is a plot of m/z against intensity (ion counts); commonly referred to as an MS spectrum. In MSI such MS spectra are taken in an array across the sample with one spectrum for each spot.

In certain, non-limiting embodiments, immunohistochemistry can be used for detecting the antimicrobial peptides selected from neutrophil defensin 1, neutrophil defensin 2 and neutrophil defensin 3. For example, a first antibody, e.g. an antibody specific for said antimicrobial peptides, can be brought into contact with a sample, e.g., a cell or a thin layer of cells, followed by washing to remove unbound antibody, and then contacted with a second, labeled antibody. Labeling can be by fluorescent markers, enzymes, such as peroxidase, avidin or radiolabeling. In certain embodiments, the first antibody can be conjugated to a fluorophore or other label for direct detection. The labeling can be analyzed visually using microscopy and the results can be recorded.

In certain embodiments, immunohistochemistry can be performed to detect a combination of the Neutrophil defensin biomarkers in the same sample to determine whether the biomarkers colocalize. The term "colocalize" as used herein refers to neutrophil defensin 1, neutrophil defensin 2 and/or neutrophil defensin 3 occurring in close proximity to each other.

Various automated sample processing, scanning and analysis systems suitable for use with immunohistochemistry are available in the art. Such systems can include automated staining (see, e.g., the Benchmark system, Ventana Medical Systems, Inc.) and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.).

Antibodies for use in the present invention include any antibody, whether natural or synthetic, full length or a fragment thereof, monoclonal or polyclonal, that binds sufficiently strongly and specifically to the biomarker that is to be detected. An antibody can have a Kd of at most about $10^{-6}$ M, $10^{-7}$ M, $10^{-8}$ M, $10^{-9}$M, $10^{-10}$M, $10^{-11}$ M and $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. Antibodies and derivatives thereof that can be used encompasses polyclonal or monoclonal antibodies, chimeric, human, humanized, primatized (CDR-grafted), veneered or single-chain antibodies, phase produced antibodies (e.g., from phage display libraries), as well as functional binding fragments, of antibodies. For example, antibody fragments capable of binding to a biomarker, or portions thereof, including, but not limited to Fv, Fab, Fab' and F(ab')2 fragments can be used. Such fragments can be produced by enzymatic cleavage or by recombinant techniques. For example, and not by way of limitation, papain or pepsin cleavage can generate Fab or F(ab')2 fragments, respectively. Other proteases with the requisite substrate specificity can also be used to generate Fab or F(ab')2 fragments. Antibodies can also be produced in a variety of truncated forms using antibody genes in which one or more stop codons have been introduced upstream of the natural stop site. For example, a chimeric gene encoding a F(ab')2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0125023 B I; Boss et al., U.S. Pat. No. 4,816,397; Boss et al., European Patent No. 0,120,694 B I; Neuberger, M. S. et al., WO 86/01533; Neuberger et al., European Patent No. 0,194,276 B1; Winter, U.S. Pat. No. 5,225,539; Winter, European Patent No. 0,239,400 B1; Queen et al., European Patent No. 0451216 B I; and Padlan et al., EP 0519596 A1. See also, Newman et al., BioTechnology, 10:1455-1460 (1992), regarding primatized antibody, and Ladner et al., U.S. Pat. No. 4,946,778 and Bird et al., Science, 242:423-426 (1988)) regarding single-chain antibodies.

In certain embodiments, agents that specifically bind to a polypeptide other than antibodies can be used, such as peptides. Peptides that specifically bind can be identified by any means known in the art, e.g., peptide phage display libraries. Generally, an agent that is capable of detecting a biomarker polypeptide, such that the presence of a biomarker is detected and/or quantitated, can be used.

Methods of Use

In certain non-limiting embodiments, the present invention provides for a method of determining whether an anti-cancer effect is likely to be produced in a cancer by immunotherapy, in particular in a treatment using PD-1/PD-L1 antagonists. In certain embodiments, a method of the present invention comprises detecting antimicrobial peptides selected from neutrophil defensin 1, neutrophil defensin 2 and neutrophil defensin 3 as biomarkers in a cancer or a sample of the cancer, where if the biomarker is localized in the cancer prior to and/or following immunotherapy, in particular following treatment with PD-1/PD-L1 antagonists, it is more likely that the immunotherapy would have an anti-cancer effect on the cancer relative to a cancer in which the biomarker is not present. In certain embodiments, the localization pattern of the biomarker may be appreciated by comparing the localization of the biomarker in the cancer to a reference sample. For example, and not by way of limitation, the reference sample can be a responsive cell. A "responsive cell" also referred to as a "responder cell" is a cancer cell which, when treated with an effective amount of a PD-1 or PD-L1 antagonist, increases expression of one or more markers of the senescent phenotype, including, but not limited to SA-b-gal, senescence-associated heterochromatin foci and elaboration of the senescence-associated secretory program and/or increases the number of ATRX foci in the nucleus and/or exhibits a decrease in MDM2 protein, relative to the level without treatment with the PD-1 or PD-L1 antagonist.

In certain embodiments, the reference sample can be a non-responsive cell. A "non-responsive cell" also referred to as a "non-responder cell" is a cancer cell, which is not a responder cell. In certain non-limiting embodiments, a non-responder cell, when treated with an amount of a PD-1/PD-L1 antagonist effective in inducing senescence in responder cells, does not increase expression of at least one marker, or at least two markers, or at least three markers, of the senescent phenotype selected from the group consisting of SA-B-gal, senescence-associated heterochromatin foci and elaboration of the senescence-associated secretory program and/or does not increase the number of ATRX foci in the nucleus and/or exhibits stable or increased levels of MDM2 protein, relative to the level without treatment with the PD-1 or PD-L1 antagonist.

A subject may be human or a non-human subject. Non-limiting examples of non-human subjects include non-human primates, dogs, cats, mice, rats, guinea pigs, rabbits, pigs, fowl, horses, cows, goats, sheep, cetaceans, etc.

An anti-cancer effect means one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, a reduction in tumor metastasis, an increase in the proportion of senescent cancer cells, an increase in the duration of time to relapse, an increase in survival and/or an increased survival without tumor progression.

In certain non-limiting embodiments, a sample includes, but is not limited to cells in culture, cell supernatants, cell lysates and tissue samples. The source of the sample may be solid tissue (e.g., from a fresh, frozen, and/or preserved organ, tissue sample, biopsy or aspirate), or cells from the individual, including circulating tumor cells. In certain non-limiting embodiments, the sample is obtained from a tumor.

In certain non-limiting embodiments, the present invention provides for a method for determining whether an anti-cancer effect is likely to be produced in a cancer by immunotherapy, in particular treatment with a PD-1 or PD-L1 antagonist, comprising, obtaining a sample of the cancer before treatment with immunotherapy, and detecting in the sample antimicrobial peptides selected from neutrophil defensin 1, neutrophil defensin 2 and neutrophil defensin 3 as biomarkers, where if one or more of the biomarkers are present in one or more cells of the cancer sample, it is more likely that immunotherapy; in particular treatment with a PD-1 or a PD-L1 antagonist would have an anti-cancer effect on the cancer relative to a cancer in which the biomarker(s) is/are not localized.

In certain non-limiting embodiments, the present invention provides for a method for producing an anti-cancer effect by immunotherapy, in particular treatment with a PD-1/PD-L1 antagonist in a subject, comprising, obtaining a sample of the cancer before or after treatment of the subject with immunotherapy, in particular treatment with a PD-1/PD-L1 antagonist, and detecting, in one or more cancer cells from the sample, one or more biomarker(s) selected from neutrophil defensin 1, neutrophil defensin 2 and neutrophil defensin 3, where if the biomarker(s) is/are localized in the one or more cancer cells from the sample, then initiating treatment of the subject with immunotherapy, in particular initiating treatment of the subject with a therapeutically effective amount of a PD-1 or PD-L1 antagonist. In certain embodiments, the method comprises detecting at least one biomarker selected from neutrophil defensin 1, neutrophil defensin 2 and neutrophil defensin 3, in one or more cancer cells, where if one of said biomarkers is present in the one or more cancer cells, then treatment of the subject with immunotherapy, in particular initiating treatment of the subject with a therapeutically effective amount of a PD-1 or PD-L1 antagonist is initiated. In certain embodiments, the presence of the foregoing combination of biomarkers can be tested, and the level of biomarker protein or mRNA may be compared to a reference responder or non-responder cell (where higher levels are found in responder than non-responder cells), and this result can be considered in determining whether to administer immunotherapy, in particular PD-1/PD-L1 antagonist therapy or not. In certain non-limiting embodiments, where none of the biomarker(s) selected from neutrophil defensin 1, neutrophil defensin 2 and neutrophil defensin 3 localize in the one or more cancer cells before or after treatment with a PD-1 or a PD-L1 antagonist, the subject from whom the cancer cells are derived is to be treated with another modality, for example, an alternative chemotherapeutic agent, biologic anti-cancer agent, or radiation therapy. A therapeutically effective amount is an amount that is able to achieve one or more of an anti-cancer effect, prolongation of survival and/or prolongation of period until relapse.

EXAMPLES

In what follows the methods and results are described that led to the characterization of the AMP's and their validation as accompanying diagnostic markers to immunotherapy as anticancer treatment.

Example 1

Material and Methods

Materials

Acetonitrile, methanol and water (LC-MS graded) were purchased form Biosolve (Valkenswaard, The Netherlands). Ethanol and 2,5-dihydroxybenzoic acid (DHB) were purchased from Merck (Overijse, Belgium). Formic acid, trifluoroacetic acid, Defensin ⅓ polyclonal goat antibody and the IFN gamma Fluman Uncoated ELISA Kit were purchased from Thermo Fisher Scientific (Merelbeke, Belgium). Hexane, xylene and hydrogen peroxide were purchased from Thermo Fisher Acros Organics (Geel, Belgium). Hematoxylin & eosin staining kit, Quick-D mounting medium and formaldehyde were purchased from Klinipath (Olen, Belgium), while ImmPRESS HRP anti-goat antibody polymer detection kit (normal horse blocking serum and secondary antigoat antibody; Vectorlabs) was obtained from Labconsult (Schaarbeek, Belgium). The synthetic peptides corresponding neutrophil defensin 1, neutrophil defensin 2 and neutrophil defensin 3 were acquired from Synpeptide Co., Ltd (Shanghai, China). Materials also include peroxidase substrate and citrate buffer.

Patients and Immunotherapy Treatment

The human biological material, both fresh frozen and formalin-fixed paraffin-embedded, used in this publication for optimizing the methods was provided by Biobank@UZA (Antwerp, Belgium; ID: BE71030031000); Belgian Virtual Tumorbank funded by the National Cancer Plan [35].

We received 27 pretreatment NSCLC (tumor tissues) formalin-fixed paraffin-embedded biopsies from Pathology Department of Antwerp University Hospital. These patients were treated with PD-1 antagonists (Pembrolizumab (14 patients, 51.9%) or Nivolumab (11 patients, 40.7%)) or PD-L1 antagonists (2 patients, Atezolizumab (7.4%)); 11 (40.7%) had a positive response to immunotherapy, whereas 16 (59.3%) had no clinical benefit after treatment. The study was approved by the Ethics Committee of the Antwerp University Hospital. For each biopsy, two tissue slices were collected on one ITO-coated glass slide for MSI analyses, two consecutive tissue slices were collected for respectively H&E staining and immunohistochemistry analysis. Three types of NSCLC types were included in the study; adenocarcinoma (14 patients), squamous (5 patients) and large cell carcinoma (2 patients). For six patients no diagnose on NSCLC tumour is available. 3 types NSCLC Fresh Frozen Tissue Sectioning and Preparation Fresh frozen human lung cancerous tissues were collected and tissue sectioning was performed on a LEICA CM1950UV cryostat to obtain slices with 14 μm thickness. To avoid optimal cutting temperature (OCT) compounds, the tissue was attached to the cryostat holder with a water droplet. Tissue sections were thaw-mounted on Indium Tin Oxide (ITO)-coated glass slides (Bruker Daltonik GmbH, Bremen, Germany) and stored at −80° C. prior to use. Tissue sections were treated according to Carnoy's washing procedure: a first rinsing step of 30 seconds in 70% EtOH, followed by 30 seconds in 100% EtOH, 90 seconds in Carnoy's fluid (EtOH: acetic acid: water (90:9:1 v: v: v)) and followed by a last rinsing part of 30 seconds in 100% EtOH. After every rinsing procedure, glass slides were tilted to maximize solvent removal. After the last rinsing part, a vacuum desiccation step of 30 minutes was performed followed by matrix deposition of 12 layers of DHB matrix (40 mg/ml_in 60/0.1 (v/v) acetonitrile/trifluoroacetic acid) by using a SunCollect pneumatic sprayer (SunChrom, Friedrichsdorf, Germany). Lastly, 0.5 μl of peptide calibration standard (Bruker Daltonik GmbH, Bremen, Germany) was spotted on top of the matrix layers, next to the tissue section for external calibration.

Mass Spectrometry Imaging

MALDI MSI data were acquired with a rapifleX tissuetyper in single TOF mode (Bruker Daltonik GmbH, Bremen, Germany), equipped with a SmartBeam 3D laser. Mass spectra were the sum of 1000 individual laser shots, with a 90% laser intensity. Mass spectral peptidomic (m/z range 800 Da-5 kDa) images were obtained in positive reflector mode with a reflector voltage of 3005V, a sample rate of 0.63 GS/s, a laser resolution of 50 μm and a raster width of 50 pm×50 μm. All the spectra are preprocessed with a Top Hat baseline algorithm for baseline subtraction and the resulting overall average spectrum of the ion image is TIC normalized in fleximaging 5.0 (Bruker Daltonik GmbH, Bremen, Germany) after recalibration in flexAnalysis 4.0 with external calibration standard. The results will be further processed in SCiLS lab 2016b (Bruker Daltonik GmbH, Bremen, Germany) and R software (Cardinal) [36].

Peptide Identification

In order to identify the MSI targets, small lung tissue blocks were collected in peptide extraction solvent consisting of methanol: water: formic acid (90:9:1 v: v: v) and shaked on ice for 30 min. The sample was kept on ice during the whole extraction procedure. First, the peptide sample was sonicated with a bar sonicator twice for 15 s each (Branson Sonifier SLPe cell disruptor). After 15 min centrifugation at 14,000 ref by 4° C., the supernatant was collected and methanol could be evaporated by using a vacuum centrifuge concentrator (Savant SPD1010 SpeedVac Concentrator, Thermo Scientific). The lipids were removed by re-extraction with n-hexane. From the remaining aqueous fraction, the peptides were concentrated using an ultra-0.5 mL 10 K centrifugal filter device (Merck) and desalting was performed by solid phase extraction with a Pierce C18 Spin Column (Thermo Scientific) according to the manufacturer's procedure. The eluted sample was again dried using the vacuum centrifuge concentrator and the sample pellets were stored at −20° C. prior to LC-MS/MS analysis.

The dried fraction(s) containing the peptides (intact, without enzymatic digestion) were dissolved in 15 mI_mobile phase A (2% acetonitrile in HPLC-grade water, 0.1% of formic acid) before separation by reversed phase C18 (RP-C18) liquid chromatography on a nanoAcquity UPLC system (Waters, Milford, MA) using an Acclaim PepMap trap column (3 μm particle size; 100 A pore size;

75 μm×20 mm, Thermo Scientific) connected to an Acclaim PepMap RSCL C18 analytical column (2 μm particle size; 100 A pore size; 50 pmc 15 cm, Thermo Scientific). A linear gradient of mobile phase B (0.1% formic acid in 98% acetonitrile and 2% water) started for 2 min with 5% mobile phase B, followed by a steep increase from 5% to 45% mobile phase B in 50 min, followed by 45% to 90% mobile phase B in 3 min and lasted extra 2 min, followed by a decrease from 90% to 1% mobile phase B in another 2 min and lasted for an extra 10 min, with a flow rate of 400 nL/min.

Identification of the three interesting antimicrobial peptides was performed on a LTQ Velos Orbitrap mass spectrometer equipped with a nanospray Flex Ion source (Thermo Fisher, Waltham, MA, USA). The high resolution mass spectrometer was set up in data-dependent acquisition mode, with an automatic gain control (AGC) target of $1\times10^5$ and the maximum injection was set to 500 ms. The precursor ion for the ETD scan was isolated in data-dependent acquisition mode with an isolation window width of 3. Activation time for reduction of this isolated ion with ETD was 200 ms and the reduced ion was selected (isolation window of 4) for further CID fragmentation in the CID MS3 step with normalized collision energy of 45% in CID (activation time of 70 ms). Fragmentation spectra of the selected ions were displayed in Xcaliber (Thermo Fisher, Waltham, MA, USA) and fragment masses and corresponding intensities were exported as CSV files for manual de novo sequencing, performed in Prosight lite [37]. Settings were 300 ppm mass accuracy for ion trap mode. Sequences were obtained in the Uniprot human database.

FFPE Tissue Sectioning and Preparation for MSI Analysis

Formalin-fixed paraffin-embedded (FFPE) human lung cancerous tissues were collected and tissue sectioning was performed on a microtome to obtain slices with 5 μm thickness. The paraffin ribbon was placed with a brush in a dFFO bath at room temperature followed by a water bath of 47-50° C. Floating paraffin ribbon sections were then mounted on Indium Tin Oxide (ITO)-coated glass slides (Bruker DaltonikGmbH, Bremen, Germany) and allowed to dry on a warming surface of 37° C. for at least 8 h [38]. Tissue sections can be stored for several months at room temperature. For each patient sample, two tissue sections were collected on one ITO-coated glass slide.

To visualize the three neutrophil defensins in FFPE tissue sections with MALDI MSI, tissue sections were deparaffinized by immersing in xylene for 5 min. This step is repeated in fresh xylene for another 5 min. Rehydration of the tissue sections was performed by immersing in graded ethanol series (twice immersing in 100% (vol/vol) ethanol for each time 1 min, once 95% (vol/vol) ethanol and once 70% (vol/vol) ethanol, each step for 1 min). The last rinsing step was twice a 3 min washing step in Milli-Q-purified water. Glass slides were air-dried for 30 min.

Matrix deposition included 12 layers of DHB matrix (40 mg/ml_in 60/0.1 (v/v) acetonitrile/trifluoroacetic acid) by using a SunCollect pneumatic sprayer (SunChrom, Friedrichsdorf, Germany) with a medium speed of the sprayer (900 mm/min). Lastly, 0.5 pi of peptide calibration standard (Bruker Daltonik GmBH, Bremen, Germany) was spotted on top of the matrix layers, next to the tissue section for external calibration.

Mass Spectrometry Imaging

MALDI MSI data were acquired with a rapifleX tissuetyper in single TOF mode (Bruker Daltonik GmBH, Bremen, Germany), equipped with a SmartBeam 3D laser. Mass spectra were the sum of 1000 individual laser shots, with a 95% laser intensity. Mass spectral neutrophil defensin (m/z range 2400-5800 Da) images were obtained in positive linear mode with a linear voltage of 3570V, a sample rate of 0.63 GS/s, a laser resolution of 100 μm and a raster width of 100 μm×100 μm. All the spectra are preprocessed with a Top Hat baseline algorithm for baseline subtraction and the resulting overall average spectrum of the ion image is TIC normalized in Fleximaging 5.0 (Bruker Daltonik GmBH, Bremen, Germany) and will be further processed in SCiLS lab 2016b (Bruker Daltonik GmBH, Bremen, Germany) and R software (Cardinal) [36].

H&E Staining

For every tissue biopsy, one section was hematoxylin and eosin (H&E) stained according to conventional protocols [39]. For previously MSI analyzed tissue sections, the matrix was removed with 70% (vol/vol) ethanol, after which the tissue was dried using a vacuum desiccator. The tissue section was then AFA (combination of alcohol, formalin and acetic acid) fixated, followed by a hematoxylin staining for 5 minutes and the eosin staining was performed for 30 seconds. The tissue section was rinsed in graded ethanol series (70% (vol/vol), 2×95% (vol/vol), 100% (vol/vol)) and in 100% (vol/vol) xylene for another 30 seconds. Coverslips were mounted with Quick-D mounting medium. The tissue sections were in this way re-evaluated by the pathologist of University Hospital of Antwerp (UZA) for confirmation of the observed regions.

Immunohistochemistry of Neutrophil Defensins

Statistical analysis using the GraphPad Prism 8.00 software (license DFG170003) was performed to determine significant differences between control and the different colitis groups within a certain model (T cell transfer or DSS). Data were analysed by the One-way Analysis of Variance (ANOVA) and non-parametric Kruskal-Wallis tests and are presented as means±standard error of mean (SEM) or boxplots (min to max), unless stated otherwise. Significance levels are indicated on the graphs by *p<0.05, <0.01, *p<0.001 and were corrected for multiple testing using the Tukey-Kramer's and Dunn's post-hoc multiple comparisons tests.

A discriminant function analysis was performed to determine whether colitis mice could be distinguished from control animals based on a set of predictor variables (i.e. the expression of cytokines, mucins or other barrier mediators). The results are depicted as scatter plots showing the two main discriminant functions (i.e. function 1 and function 2) with the according main predictor variables summarized in a table. Furthermore, a multiple linear regression analysis was carried out to investigate associations (1) between changes in barrier integrity and the expression of mucins, cytokines and barrier mediators; (2) between the expression of mucins, cytokines and barrier mediators. Scatter plots are shown distinguishing between different experimental groups with the corresponding p-value of the regression model. A p-value below 0.05 was considered statistically significant. These analyses were performed using IBM SPSS Statistics 24 software.

Example 2

Results

MALDI Mass Spectrometry Imaging for Predictive Biomarker Discovery

We have demonstrated earlier that MALDI mass spectrometry imaging (MSI) has been recognized as a powerful tool to visualize the NSCLC tumor microenvironment based on the endogenous peptidomic profile (m/z range 800-5000 Da) without causing delocalization of these analytes [24]. The advantage that the measurements are taken in a predefined order, allows us to analyze the distribution of all the individual m/z peaks, thus of all the biomolecules present in the tissue sample. Differential expression analysis of peptides in tumor versus nontumor region, revealed two interesting peptides m/z 3369.5 and m/z 3440.6. These show a specific distribution, with a high expression in the nontumor region, a very high expression at the interaction border between the nontumor and tumor region and finally a very low to absent expression further in the tumor region, as displayed in FIG. 1, which is an example of human squamous cell carcinoma fresh frozen lung tissue biopsy.

Figure 1C:
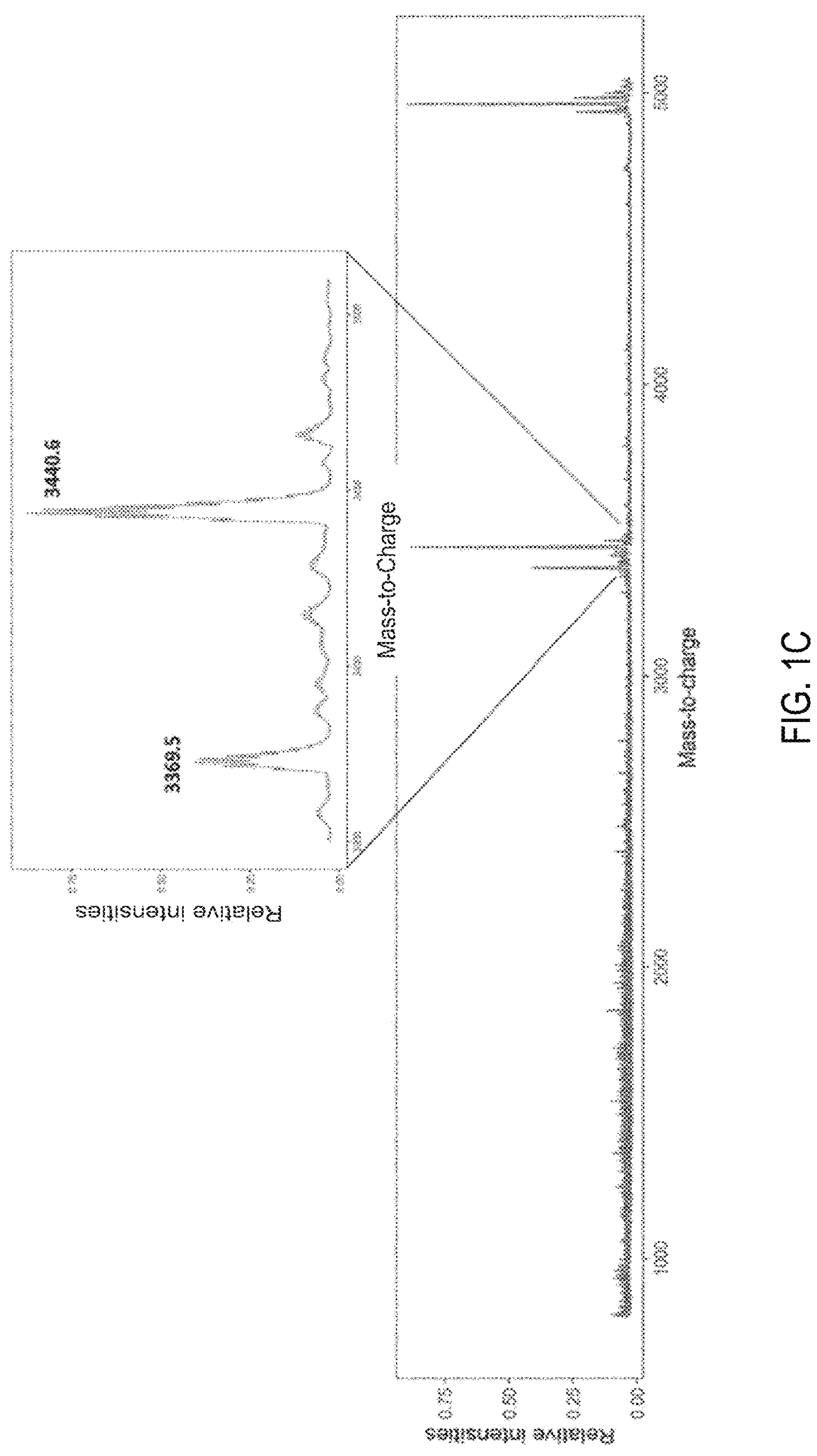
Figures 2A, 2B:
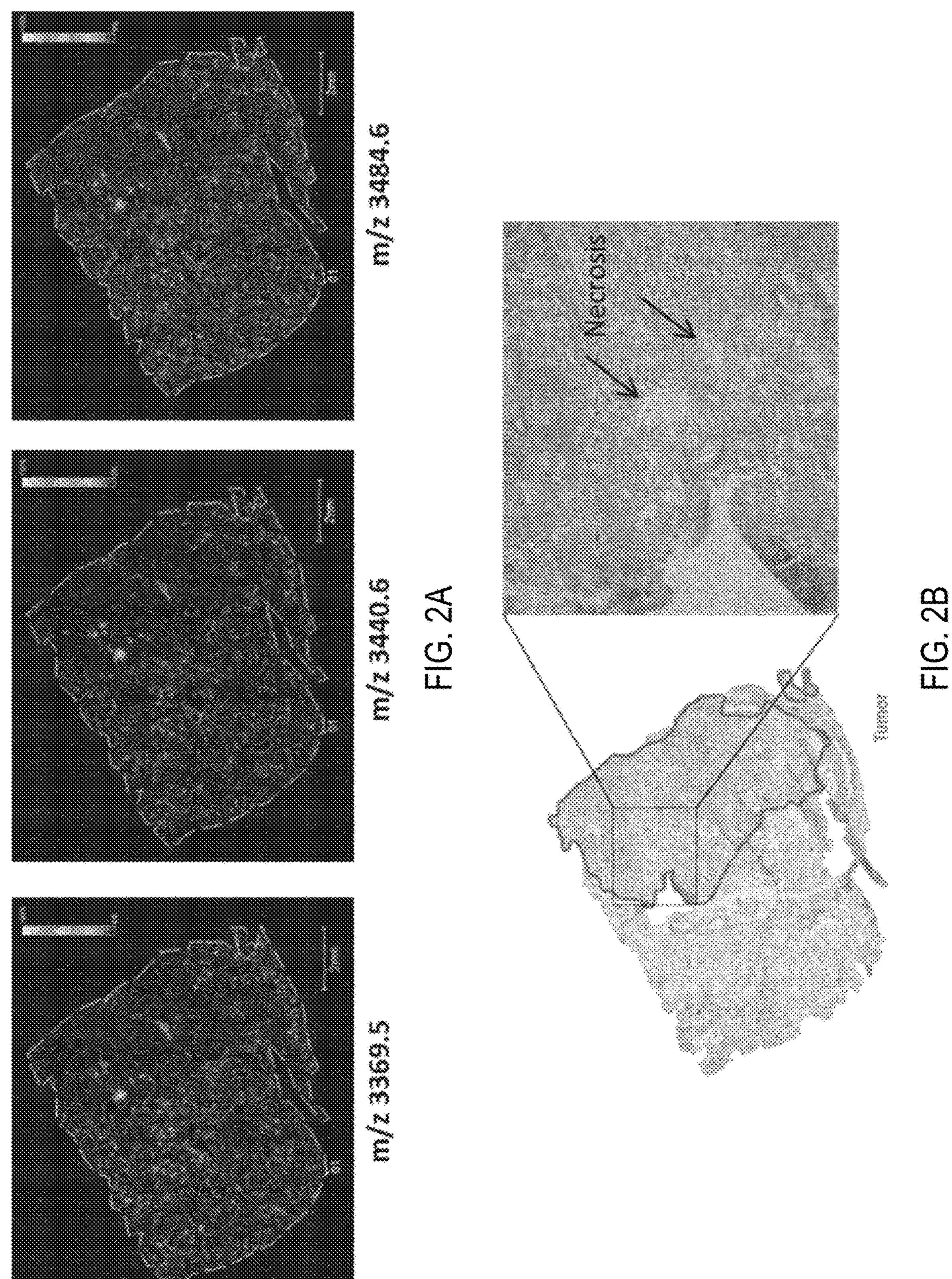
FIGS. 2A-2C: MALDI mass spectrometry imaging (MSI) showing the distribution of three peptides of interest m/z 3369.5, m/z 3440.6 and m/z 3484.6 in fresh frozen human adenocarcinoma lung cancerous tissue (FIG. 2A) with adjacent H&E stained reference tissue (FIG. 2B), obtained after MALDI MSI.
Figure 2C:
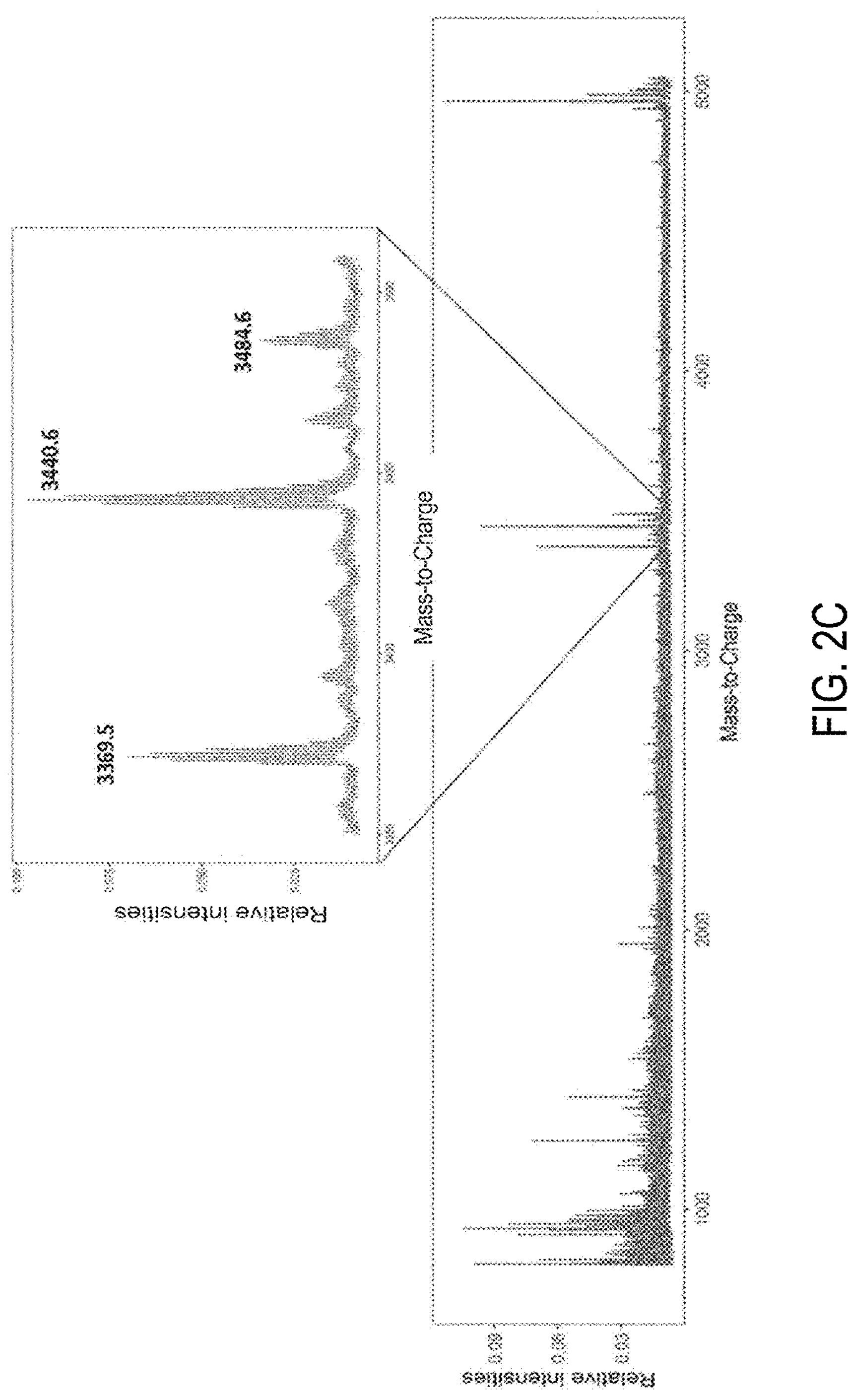

In a fresh frozen lung tissue adenocarcinoma example, besides the two peptides identified in the squamous cell carcinoma, a third peptide m/z 3484.6 with similar distribution was observed (see FIG. 2A), although the expression at the interaction border is not as high as in FIG. 1. Further, three spots with high expression of these three peptides are observed in the tumor region and these regions are necrotic regions, which is zoomed out in the H&E staining in FIG. 2B.

Peptides of Interest are Identified as Neutrophil Defensin 1, Neutrophil Defensin 2 and Neutrophil Defensin 3

Figures 3A, 3B, 3C:
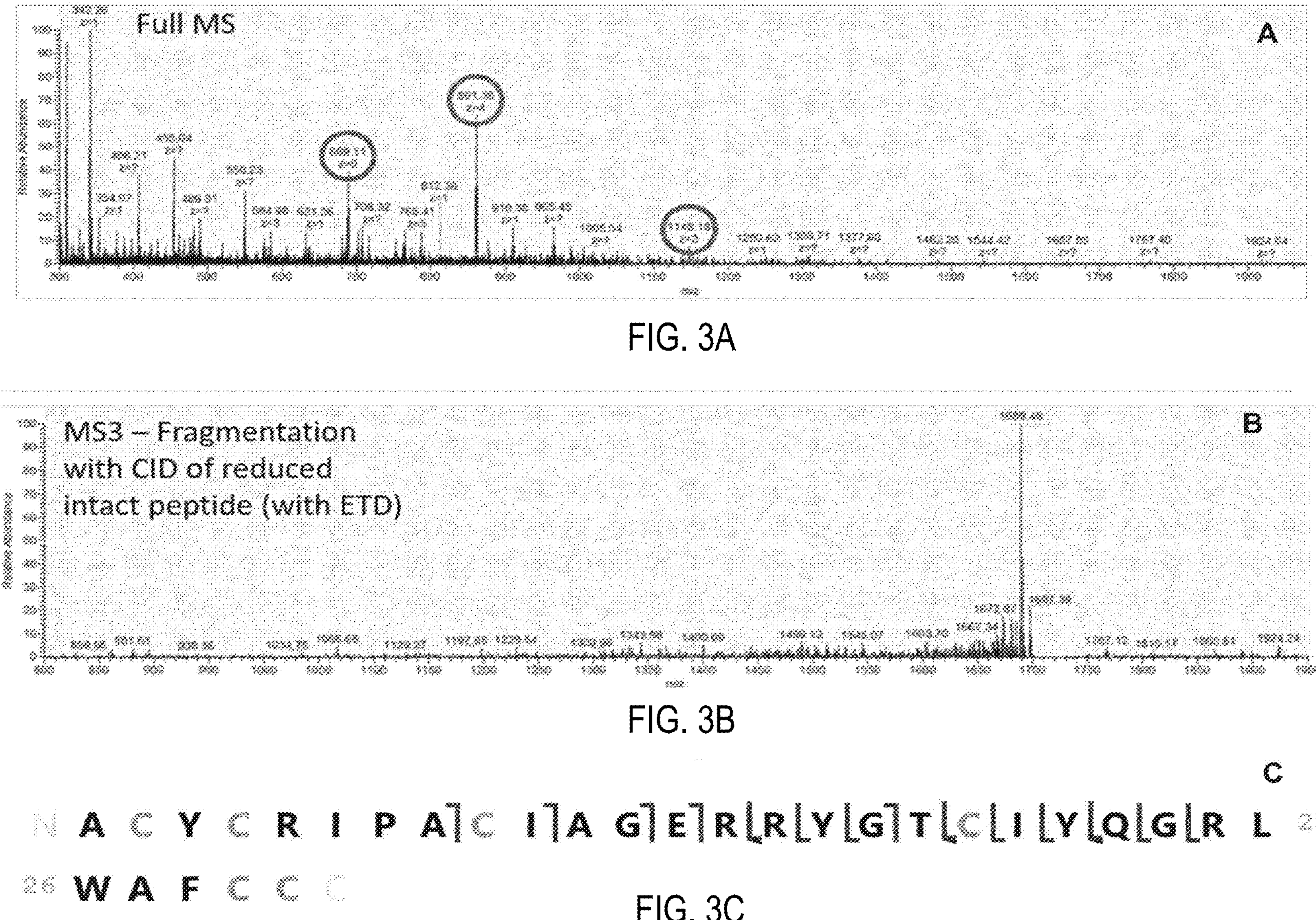
FIGS. 3A-3C: Mass spectra and annotated sequence of Neutrophil defensin 1.
Figures 7A, 7B:
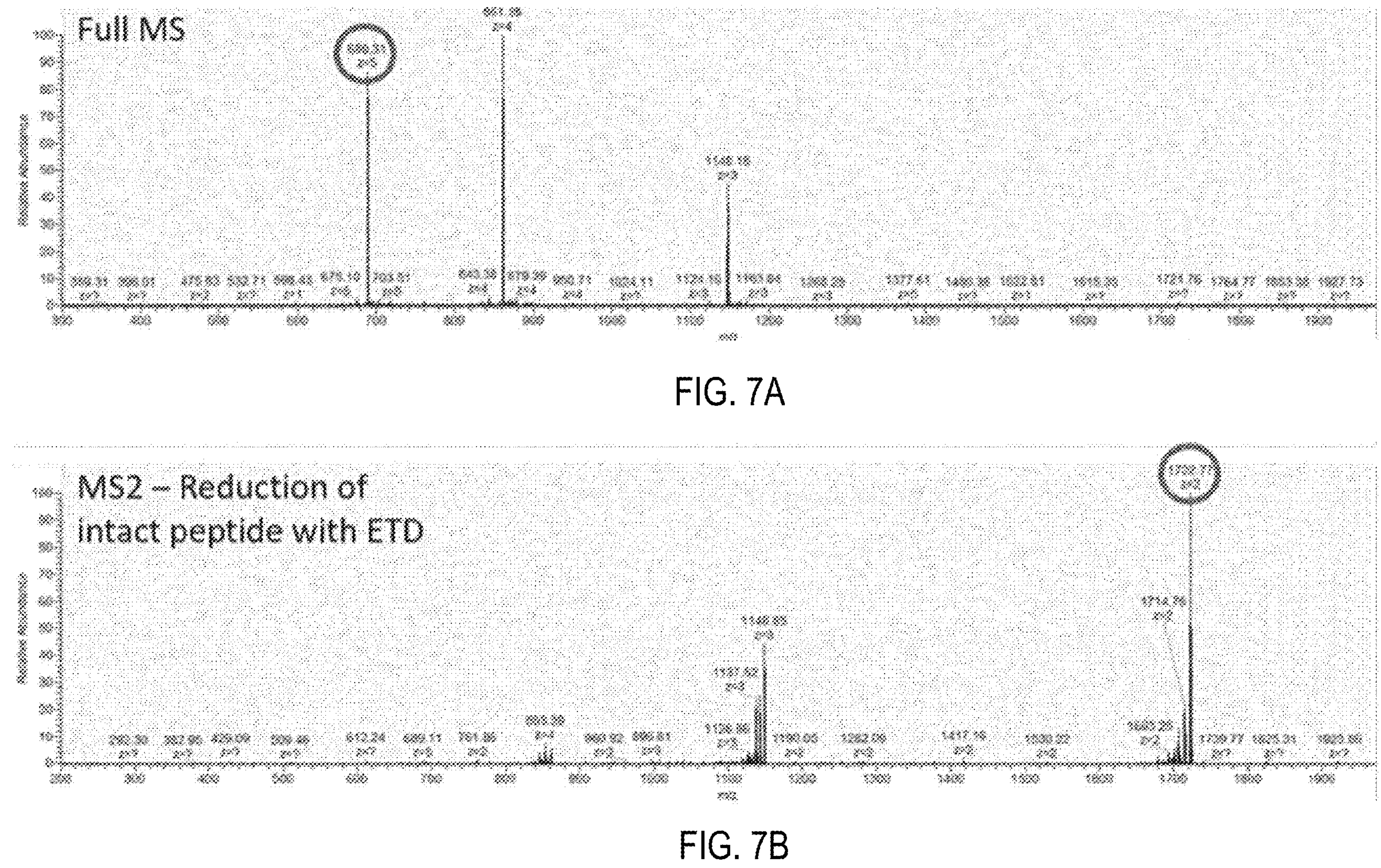
FIGS. 7A-7D: Mass spectra and annotated sequence of synthetic peptide corresponding for Neutrophil defensin 1.
Figures 7C, 7D:
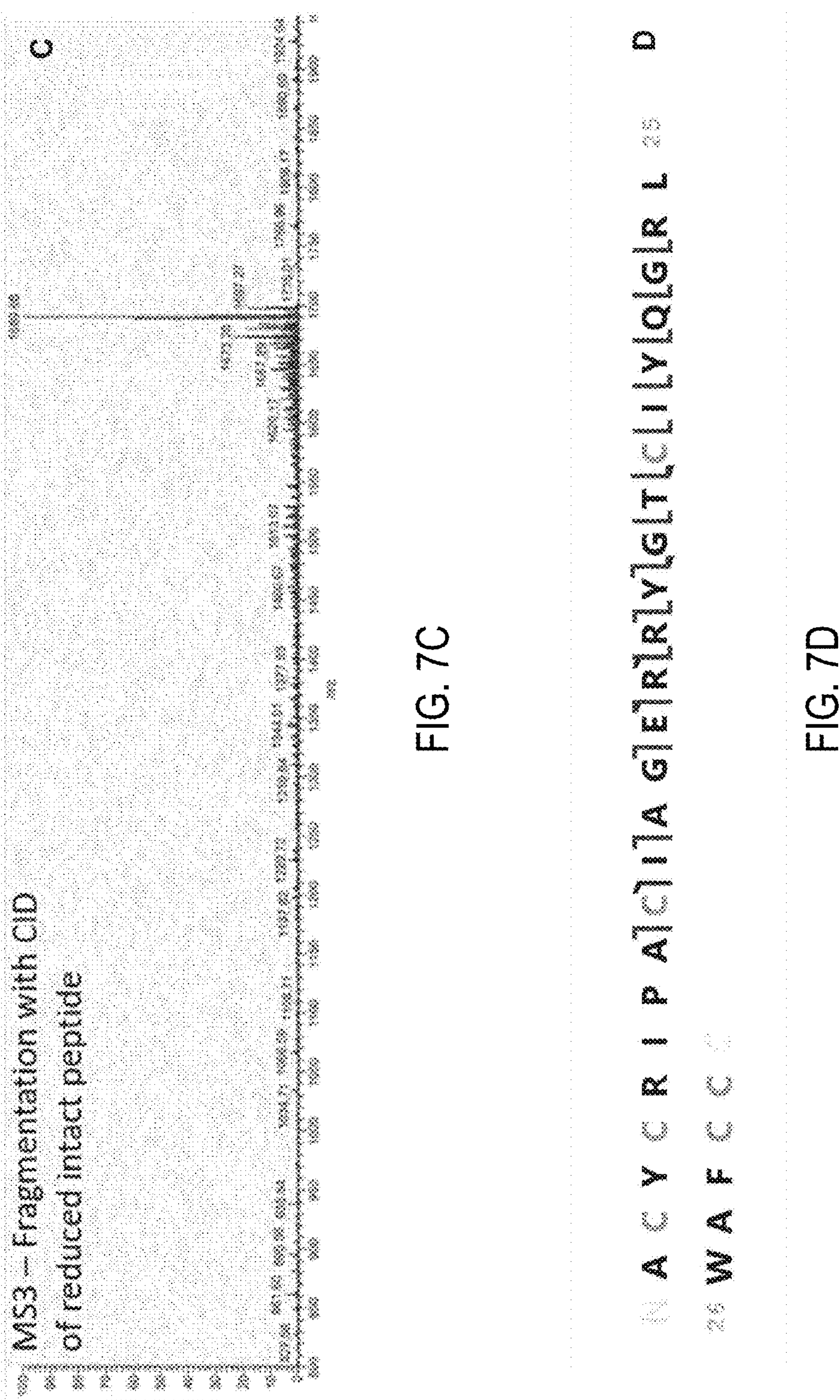

Identification of these three peptides of interest was not possible with top-down peptidomics as we performed earlier for identification of other MALDI MSI targets [24]. The precursors for these peptides were selected, but corresponding fragmentation spectra could not be acquired, possibly due to disulfide linkages, one frequently occurring post-translational modification (PTM) for correct folding and peptide or protein stability [40]. To avoid reduction and alkylation steps, which complicates the direct linkage of m/z values of intact molecules observed with MALDI MSI, we developed a method where disulfide bridges containing peptides were reduced within a high-resolution mass spectrometer with electron-transfer dissociation (ETD) in a MS2 scan (see more detailed in supplementary materials), as it has been proven that ETD can induce disulfide bond cleavage [40]-[42]. The resulting reduced intact peptide is then immediately selected for fragmentation with collision-induced dissociation (CID) for reliable identification (see FIGS. 3B-3C). Fragments can be a mixture of b and y ions, obtained by CID fragmentation, and c and z ions, obtained by ETD fragmentation. Matching the observed fragments with the theoretical fragments was performed in Prosight lite [37] with 300 ppm mass accuracy for the deconvoluted fragmentation spectra, which is sufficient for fragmentation data obtained in ion trap mode. In this way, we have identified m/z 3440.6 as neutrophil defensin 1, presented in FIG. 3C and table 1. These findings were confirmed with the synthetic peptide corresponding neutrophil defensin 1 (data shown in FIG. 7). The two other peptides of interest were identified in the same way as neutrophil defensin 2 and 3 (List of annotated deconvoluted fragments of DEFA2 and DEFA3 is shown in Tables 2 and 3 below). These three peptides differ from each other in only a single amino acid

TABLE 1

List of annotated deconvoluted fragments (mixture of b, c, y and z ions), which are aligned to neutrophil defensin 1, performed in Prosight lite with 300 ppm mass accuracy to accommodate for low mass accuracy for ion trap mode.
Neutrophil defensin 1
ACYCRIPACIAGERRYGTCIYQGRLWAFCC
m/z 688.91; z = 5; Mass 3439.55 Da
Retention time 31.38 min

| Name | Ion Type | Ion Number | Theoretical Mass | Observed Mass | Mass Difference (Da) | Mass Difference (ppm) |
|---|---|---|---|---|---|---|
| C8 | C | 8 | 894.42016 | 894.580505 | 0.160345 | 179.2725692 |
| C10 | C | 10 | 1110.51341 | 1110.714966 | 0.201556 | 181.4980334 |
| C12 | C | 12 | 1238.57198 | 1238.811157 | 0.239177 | 193.1070651 |
| C13 | C | 13 | 1367.61457 | 1367.952881 | 0.338311 | 247.3730592 |
| C17 | C | 17 | 1899.90158 | 1899.846436 | −0.055144 | −29.02466137 |
| Y9 | Y | 9 | 1082.478985 | 1082.668701 | 0.189716 | 175.2606772 |
| Y12 | Y | 12 | 1461.635565 | 1461.895508 | 0.259943 | 177.843921 |
| Y16 | Y | 16 | 1938.869145 | 1939.321045 | 0.4519 | 233.0740067 |
| Z7 | Z | 7 | 881.38018 | 881.510986 | 0.130806 | 148.4104169 |
| Z8 | Z | 8 | 938.40164 | 938.560364 | 0.158724 | 169.1429269 |
| Z9 | Z | 9 | 1066.46022 | 1066.680298 | 0.220078 | 206.3630653 |
| Z10 | Z | 10 | 1229.52355 | 1229.841064 | 0.317514 | 258.2414953 |
| Z11 | Z | 11 | 1342.60761 | 1342.919067 | 0.311457 | 231.9791707 |
| Z12 | Z | 12 | 1445.6168 | 1446.032227 | 0.415427 | 287.3700693 |
| Z14 | Z | 14 | 1603.68594 | 1603.703613 | 0.017673 | 11.02023754 |
| Z15 | Z | 15 | 1766.74927 | 1767.123413 | 0.374143 | 211.769155 |
| Z16 | Z | 16 | 1922.85038 | 1923.075928 | 0.225548 | 117.2987781 |

TABLE 2

List of annotated deconvoluted fragments (mixture of b, c, y and z ions) in the lung cancerous tissue sample, which are aligned to neutrophil defensin 2, performed in Prosight lite with 300 ppm mass accuracy to accommodate for low mass accuracy for ion trap mode.
Neutrophil defensin 2
CYCRIPACIAGERRYGTCIYQGRLWAFCC
m/z 674.70; z = 5; Mass 3368.50 Da
Retention time 32.42 min

| Name | Ion Type | Ion Number | Theoretical Mass | Observed Mass | Mass Difference (Da) | Mass Difference (ppm) |
|---|---|---|---|---|---|---|
| C7 | C | 7 | 823.38305 | 823.594604 | 0.211554 | 256.9326634 |
| C12 | C | 12 | 1296.57746 | 1296.84729 | 0.26983 | 208.109433 |
| C13 | C | 13 | 1452.67857 | 1452.891113 | 0.212543 | 146.3111003 |
| C14 | C | 14 | 1608.77968 | 1609.172974 | 0.393294 | 244.4672847 |
| Y11 | Y | 11 | 1358.626375 | 1358.781738 | 0.155363 | 114.3529986 |
| Y13 | Y | 13 | 1562.683245 | 1563.130005 | 0.44676 | 285.8928714 |
| Z7 | Z | 7 | 881.38018 | 881.598877 | 0.218697 | 248.1301542 |
| Z8 | Z | 8 | 938.40164 | 938.545715 | 0.144075 | 153.5323404 |
| Z9 | Z | 9 | 1066.46022 | 1066.759644 | 0.299424 | 280.7643402 |
| Z10 | Z | 10 | 1229.52355 | 1229.793579 | 0.270029 | 219.6208442 |
| Z11 | Z | 11 | 1342.60761 | 1342.879272 | 0.271662 | 202.3390885 |
| Z12 | Z | 12 | 1445.6168 | 1445.903931 | 0.287131 | 198.6217924 |
| Z13 | Z | 13 | 1546.66448 | 1546.879395 | 0.214915 | 138.9538602 |
| Z14 | Z | 14 | 1603.68594 | 1603.933228 | 0.247288 | 154.1997681 |
| Z15 | Z | 15 | 1766.74927 | 1767.046387 | 0.297117 | 168.1715708 |
| Z16 | Z | 16 | 1922.85038 | 1923.084229 | 0.233849 | 121.6158066 |

TABLE 3

List of annotated deconvoluted fragments (mixture of b, c, y and z ions) in the lung cancerous tissue sample, which are aligned to neutrophil defensin 3, performed in Prosight lite with 300 ppm mass accuracy to accommodate for low mass accuracy for ion trap mode.
Neutrophil defensin 3
DCYCRIPACIAGERRYGTCIYQGRLWAFCC
m/z 697.71; z = 5; Mass 3483.55 Da
Retention time 32.21 min

| Name | Ion Type | Ion Number | Theoretical Mass | Observed Mass | Mass Difference (Da) | Mass Difference (ppm) |
|---|---|---|---|---|---|---|
| B15 | B | 15 | 1706.78032 | 1706.319824 | −0.460496 | −269.8039077 |
| B15 | B | 15 | 1706.78032 | 1707.215088 | 0.434768 | 254.7299116 |
| B17 | B | 17 | 1926.86511 | 1927.2146 | 0.34949 | 181.3775122 |
| C8 | C | 8 | 938.40999 | 938.541016 | 0.131026 | 139.6255383 |
| C11 | C | 11 | 1225.54035 | 1225.755737 | 0.215387 | 175.7485994 |
| C12 | C | 12 | 1282.56181 | 1282.87561 | 0.3138 | 244.6665709 |
| C13 | C | 13 | 1411.6044 | 1411.87915 | 0.27475 | 194.6366843 |
| C14 | C | 14 | 1567.70551 | 1568.07251 | 0.367 | 234.1000894 |
| Y11 | Y | 11 | 1358.626375 | 1358.895508 | 0.269133 | 198.0919883 |
| Y12 | Y | 12 | 1461.635565 | 1461.801147 | 0.165582 | 113.2854208 |
| Y13 | Y | 13 | 1562.683245 | 1563.066528 | 0.383283 | 245.2723552 |
| Y14 | Y | 14 | 1619.704705 | 1619.254883 | −0.449822 | −277.718524 |
| Y14 | Y | 14 | 1619.704705 | 1620.119751 | 0.415046 | 256.2479437 |
| Z7 | Z | 7 | 881.38018 | 881.528442 | 0.148262 | 168.2157182 |
| Z8 | Z | 8 | 938.40164 | 938.541016 | 0.139376 | 148.5248896 |
| Z9 | Z | 9 | 1066.46022 | 1066.593506 | 0.133286 | 124.9798141 |
| Z10 | Z | 10 | 1229.52355 | 1229.714233 | 0.190683 | 155.0869034 |
| Z11 | Z | 11 | 1342.60761 | 1342.716797 | 0.109187 | 81.32458001 |
| Z12 | Z | 12 | 1445.6168 | 1445.846436 | 0.229636 | 158.8498418 |
| Z13 | Z | 13 | 1546.66448 | 1546.86499 | 0.20051 | 129.6402695 |
| Z14 | Z | 14 | 1603.68594 | 1603.986938 | 0.300998 | 187.6913631 |
| Z15 | Z | 15 | 1766.74927 | 1767.060303 | 0.311033 | 176.0481837 |
| Z16 | Z | 16 | 1922.85038 | 1922.958496 | 0.108116 | 56.22694367 |

The identified neutrophil defensins 1, 2 and 3, also known as human alpha defensin 1, 2 and 3 or human neutrophil peptide (HNP) 1, 2 and 3, belong to the so-called antimicrobial peptides (AMPs) [43], [44]. Members of this peptide family are known to be cytotoxic, mainly for bacteria and are produced and released from the granules of neutrophils as response to microbial invasions, to fight and eliminate bacterial cells and/or viruses [43]. More interestingly for this study, neutrophil defensin 1 is associated with tumor necrosis (see also FIGS. 5A-5B) when expressed intratumorally, which makes this endogenous peptide a potential prognostic biomarker in cancer [43], [45], [46]. Also inhibition of tumor angiogenesis is reported by expression of neutrophil defensin 1 [44]. The three identified neutrophil defensins are also suggested as potential molecular markers of response, as defensin overexpression is associated with a response of breast cancer patients to neoadjuvant taxane-based therapies [47]. The most important assumption according to this study is the homozygous deletion of the defensin genes in human cancers, which is associated with Ipilimumab (anti CTLA-4 immunotherapy) resistance [48].

Considering these interesting assumptions and the very specific localization of the neutrophil defensins within lung tissues we observed, further physiological research to evaluate the potential relationship with anti PD-1/PD-L1 immunotherapy (Pembrolizumab, Nivolumab and Atezolizumab) response in NSCLC patients is required.

Figure 4A:
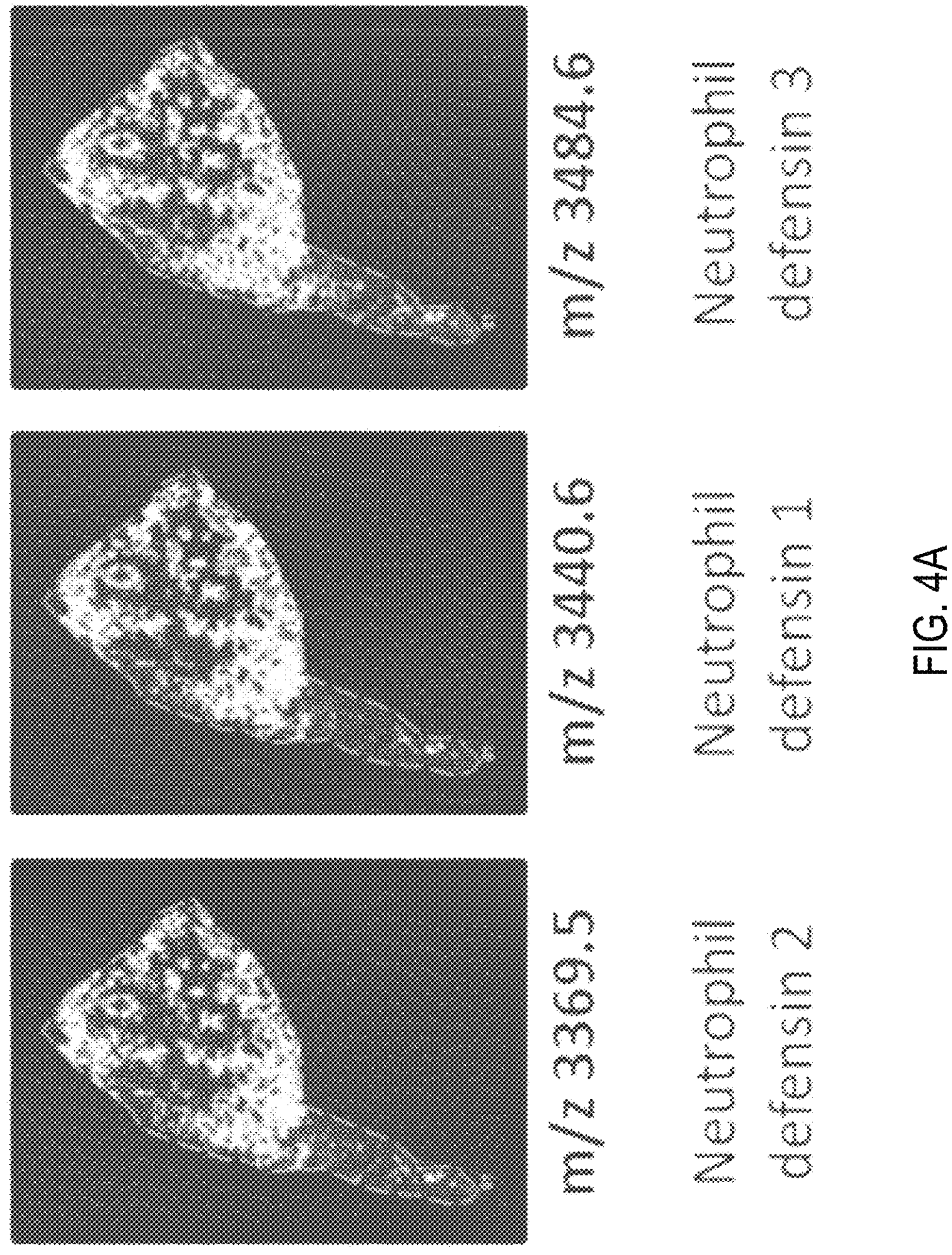
FIGS. 4A-4B: Average MALDI MSI mass spectrum in FFPE lung tissues, in which neutrophil defensin 1, neutrophil defensin 2 and neutrophil defensin 3 were observed (FIG. 4B).
Figure 4B:
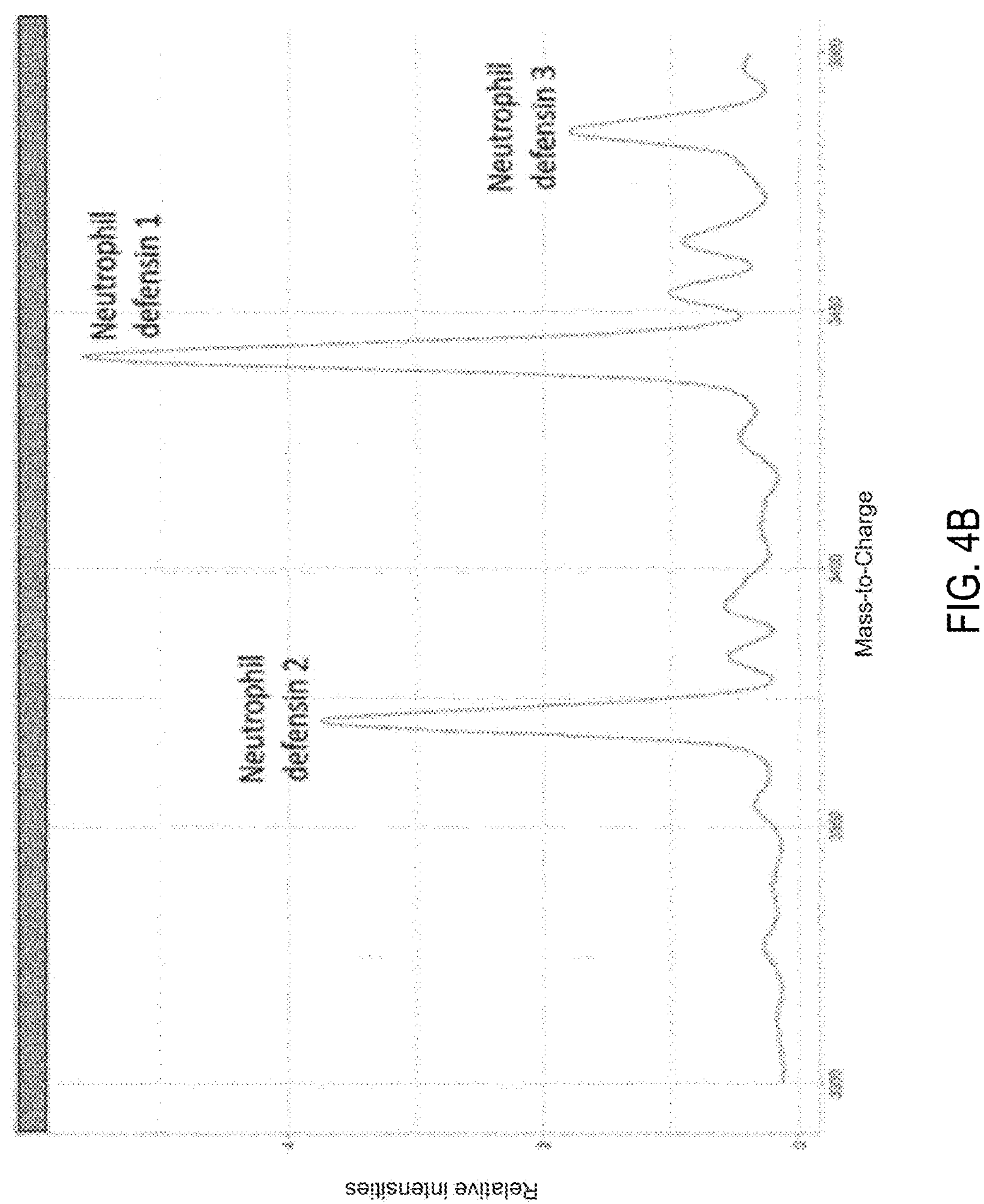
Figures 5A, 5B:
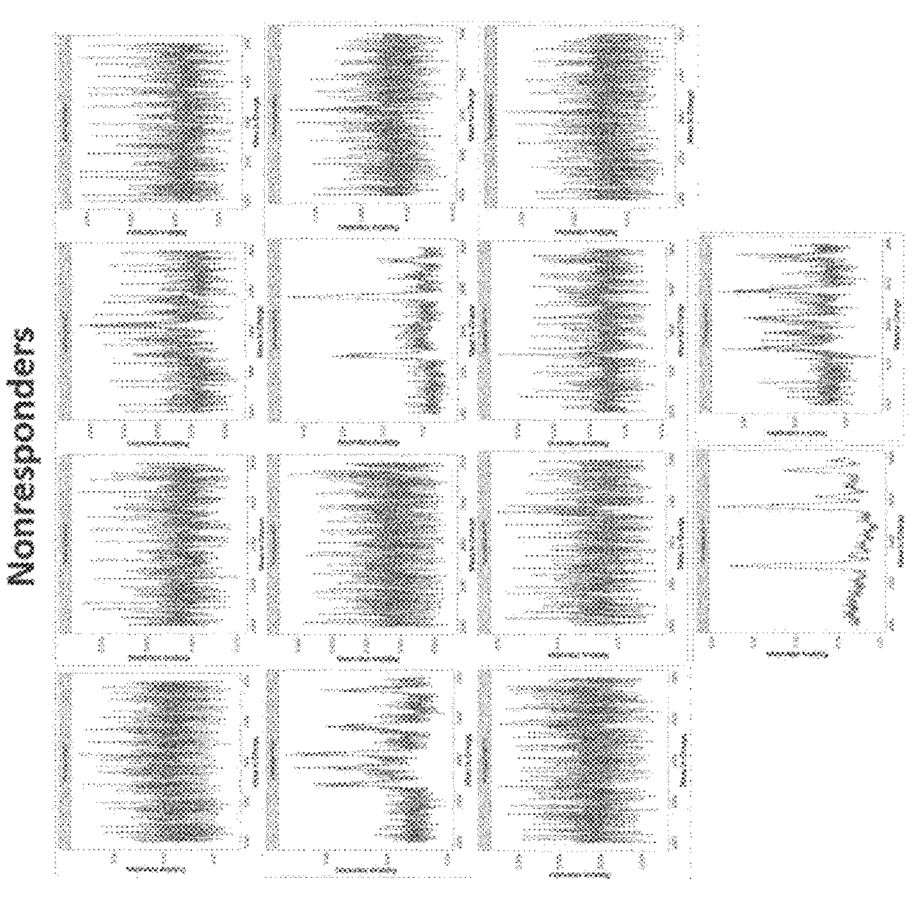
FIGS. 5A-5B: Average mass spectra of pretreatment biopsies of NSCLC patients who received immunotherapy treatment (Pembrolizumab, Nivolumab or Atezolizumab) obtained with MALDI mass spectrometry imaging on FFPE lung cancerous tissues.

Neutrophil Defensins as Pretreatment Biomarkers for Immunotherapy Treatment Response To evaluate the potential relationship between these neutrophil defensins and anti PD-1/PD-L1 immunotherapy response in NSCLC patients, AMP profiling was performed on pretreatment biopsies of NSCLC patients treated with immunotherapy. So far, MALDI MSI data was limited in this study to fresh frozen lung tissue biopsies, as visualization of intact immune-related factors is of interest. Due to formation of inter- and intra-molecular cross-linking of proteins, analysis of intact peptides and proteins leads to difficulties in formalin-fixed paraffin-embedded (FFPE) lung tissue biopsies by formalin fixation [49]. Although, histological and morphological integrity is preserved in FFPE tissue specimens, which makes these type of tissues suitable for pathological analysis [50]. In addition, FFPE tissue blocks can be long-termed stored by room temperature without quality reduction, which has led to archives of pre-treatment biopsies from large cohorts of patients [51]. The identified neutrophil defensins are relatively small and visualization of these intact three AMPs in FFPE lung tissue biopsies was possible after minimal sample preparation steps (see FIG. 4); paraffin was removed by xylene and rehydration of the tissue was performed with graded ethanol series [38]. Critical sample preparation step is involved in tissue slicing of FFPE tissue, where 5 μm thick tissue slices were attached to ITO-slides during a heating step of at least 8 h at 37° C. The resulting average mass spectrum with the three neutrophil defensins is depicted in FIGS. 5A-5B, as well as the distribution of each neutrophil defensin individually.

This notable outcome has led to the availability of 27 FFPE tumor biopsies (Bioban k@UZA) of NSCLC patients who received immunotherapy as treatment. For every patient within these two patient cohorts, clinical outcome of immunotherapy was evaluated. Average MALDI MSI profiles of each FFPE tumor biopsy is demonstrated in FIGS. 5A-5B and these average MALDI MSI spectra from 11 responding patients (FIG. 5B) and 16 nonresponding patients (FIG. 5A) to immunotherapy treatment were compared on the presence or absence of neutrophil defensin 1, neutrophil defensin 2 and neutrophil defensin 3. This figure shows the presence of the AMP's in the biopsies of the responders, and their absence in the biopsies of the non-responders.

Validation of Biomarkers with Immunohistochemistry Staining (IHC)

As we have not yet developed a method to identify peptides and proteins directly from a FFPE tissue section, we validated the obtained MALDI MSI results with immunohistochemistry analyses (IHC). Immunohistochemistry of the neutrophil defensins was performed with a defensin ⅓ polyclonal antibody, which cannot make the distinction between the three neutrophil defensins, because these only differ from each other in one single amino acid and the antibody corresponds only one small specific sequence within this peptide. With MALDI MSI, we can distinguish the three different neutrophil defensins, based upon their difference in mass due to the difference in amino acid composition.

Figures 8A, 8B:
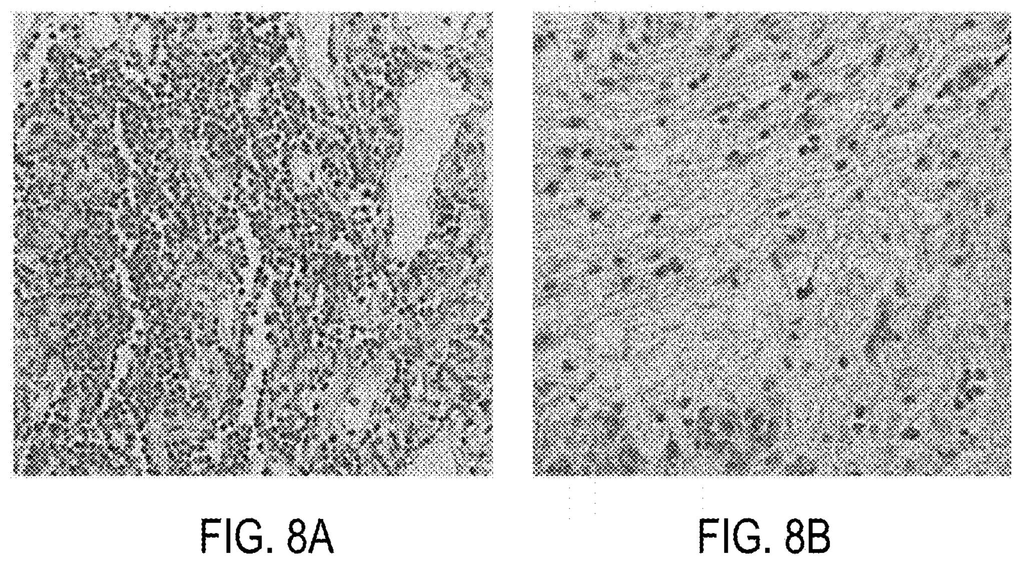
FIGS. 8A-8B: Examples of immunohistochemistry (IHC) results for defensin ⅓ antibody staining.

Immunohistochemical studies demonstrated the presence of (one of) these neutrophil defensins in positive controls, while no staining of the neutrophil defensins was observed in the neutrophil defensin negative control (see FIGS. 8A-8B).

Figure 6A:
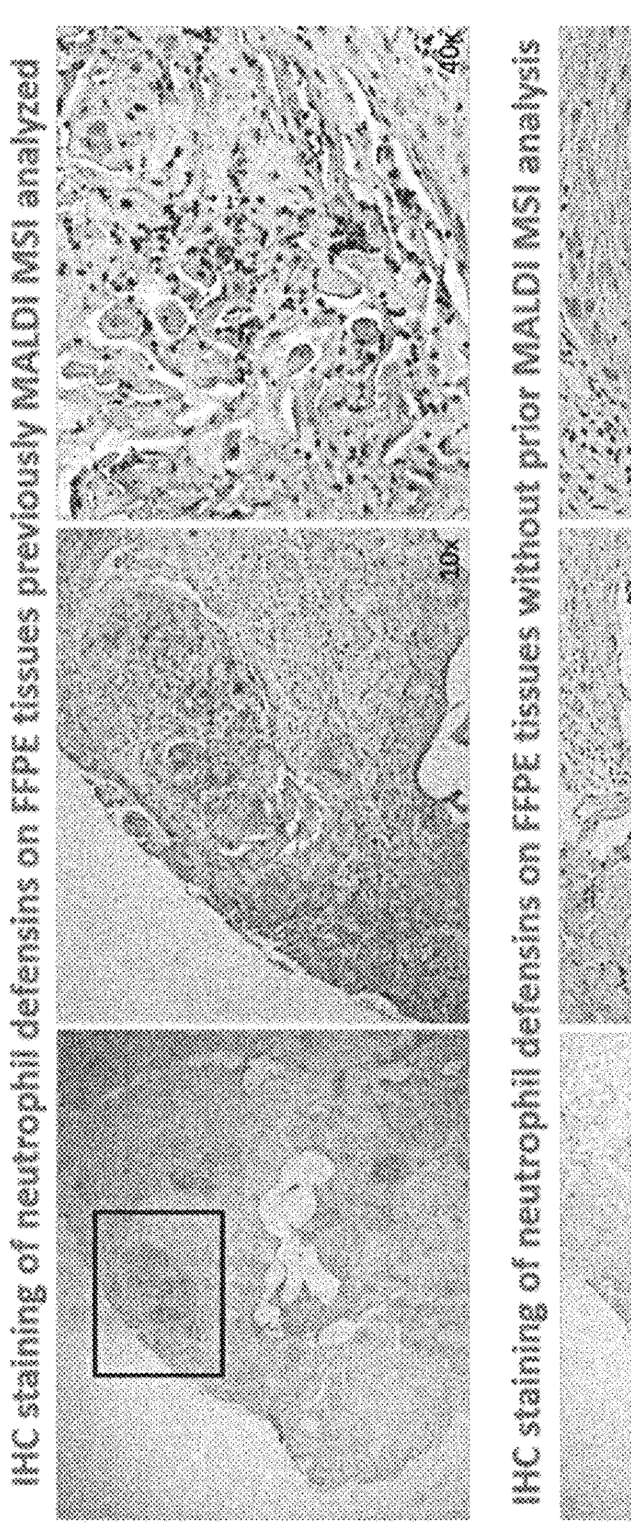
FIGS. 6A-6B: Comparison of defensin ⅓ antibody staining on FFPE tissue sections analyzed by MALDI MSI previously and without prior MALDI MSI analysis. This antibody is not able to differentiate the 3 different defensins thus staining all three
Figure 6A:
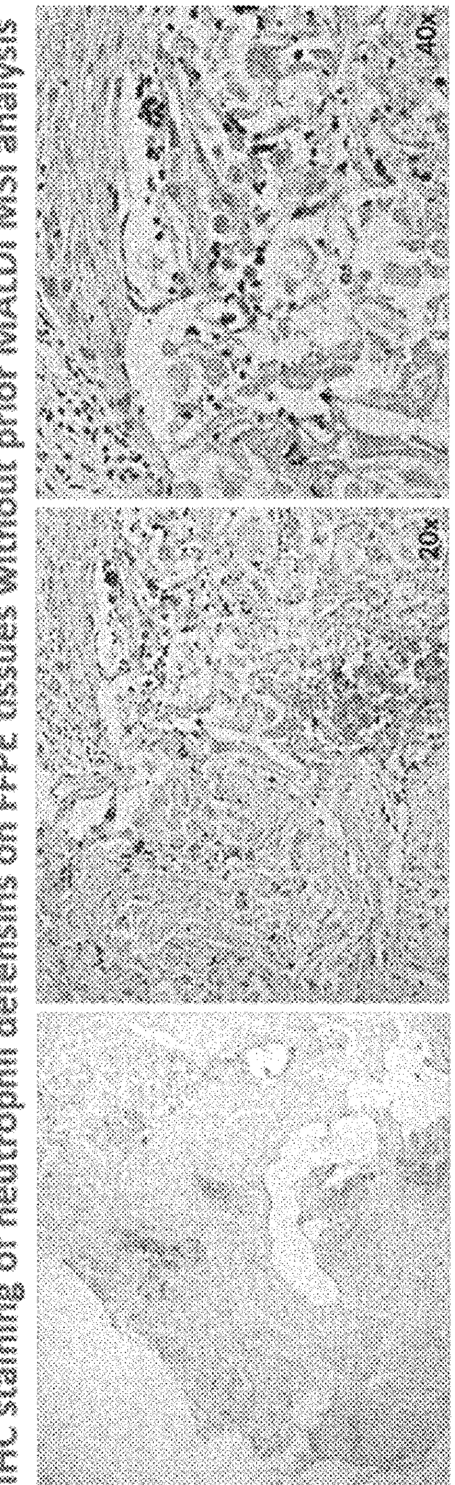
Figure 6B:
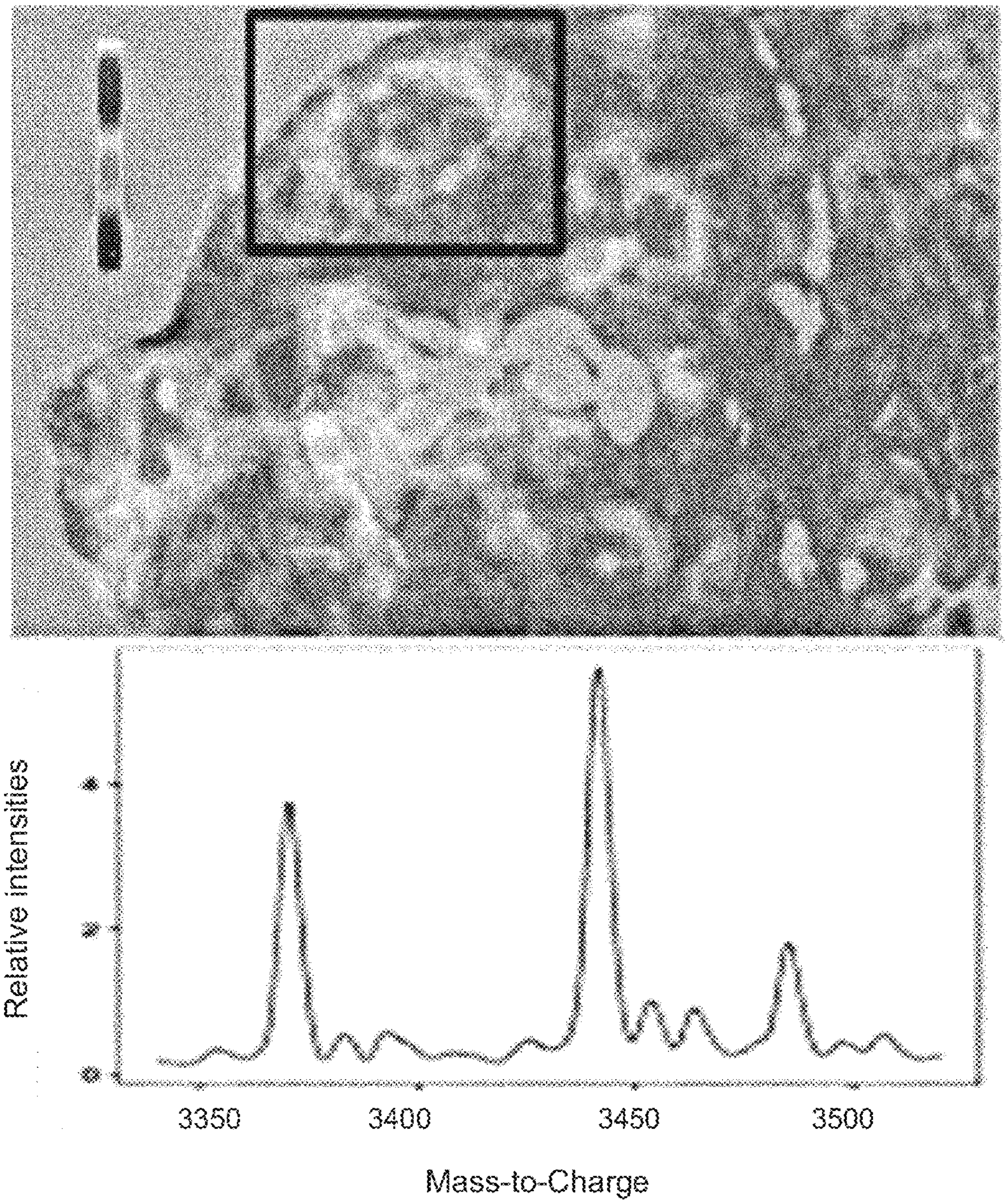

We illustrated in FIG. 6A that IHC is feasible on FFPE tissue section previously analyzed with MALDI MSI, after matrix removal with an alcohol wash. Also, the same IHC protocol was performed on a consecutive FFPE tissue section with no prior MSI analysis. From this, we can conclude that there is no change in staining intensity compared to IHC performed on tissue sections with and without prior MSI analysis. This remarkable result has the great potential to match peptide/protein information without additional consumption of tissue material [34], as pretreatment tissue specimens can be scarce. Another more important advantage for this study is the reliable validation of the peptide results obtained after MALDI MSI. Very specific MSI regions with high neutrophil defensin expression can be overlaid in this way with IHC regions, obtained after staining with the defensin ⅓ polyclonal antibody on the FFPE tissue previously analyzed with MALDI MSI, as presented in FIG. 6A.

In this way, we validated each tumor biopsy for the presence or absence of the neutrophil defensins (data not shown), and a pathologist validated each tumor pretreatment biopsy for the presence or absence of the neutrophil defensins on both the tumor cells and immune cells (Table 4).

TABLE 4

The percentage of neutrophil defensin positive cells for each NSCLC patient individually, determined with IHC. Neutrophil defensin expression on tumor cells and immune cells

| | Responding patients | | | Nonresponding patients | | | |
|---|---|---|---|---|---|---|---|
| Tumor Cells | 0% | 12.5% | 2.0% | 0% | 0% | 0% | 0% |
| Immune Cells | 1.5% | 5.0% | 5.0% | 0% | 0% | 0% | 0% |
| Tumor Cells | 25.0% | 0% | 0% | 0% | 1.5% | 0% | 5.0% |
| Immune Cells | 0% | 0% | 7.5% | 0% | 35.0% | 1.5% | 0% |
| Tumor Cells | 3.5% | 5.0% | 2.0% | 0% | 0% | 0% | 1.5% |
| Immune Cells | 35.0% | 10.0% | 2.0% | 0% | 0% | 0% | 0% |
| Tumor Cells | | | | 0% | 0% | 10.0% | 0% |
| Immune Cells | | | | 0% | 50.0% | 10.0% | 0% |

When we performed a Mann-Whitney U test on these data, it showed indeed a significant association between the percentage of neutrophil defensin positive tumor cells and the response to immunotherapy (p=0.027). This association was also observed when the neutrophil defensins were expressed on immune cells (p=0.043).

We constructed a receiver operating characteristic (ROC) curve for the percentage of neutrophil defensin expression in the immunotherapy responder and non-responder groups. The optimal sensitivity and specificity for the detection of responders was obtained with a cut-off of 1.75%. Based on this cut-off value, neutrophil defensin expression was considered positive if there was at least a 2% expression on tumor or immune cells. With this new positivity percentage, ×2-tests revealed an even more significant difference between responding and nonresponding NSCLC patients based upon tumor cells (p=0.01) and immune cells (p=0.031).

With the combined use of PD-L1 and the three neutrophil defensins as biomarker, only 16% of the patients (25 NSCLC patients in total) included in the study were incorrectly stratified, whereas with PD-L1 expression as sole prospective biomarker, 64% was wrongly stratified as responder. Measuring the therapeutic response by using both MSI and IHC in NSCLC patients who received immunotherapy thus greatly contributes to a more informative therapy decision and administration, resulting in better clinical response and avoiding unnecessary costs and toxicities in patients who will not clinically respond.

Association of Neutrophil Defensins Expression with Clinicopathological Characteristics Using the aforementioned positivity percentage of at least 2% neutrophil defensin expression on respectively tumor and immune cells, we checked association with other clinicopathological characteristics. The results are summarized in table 5, and for the current set of 25 samples a strong association Is indeed only shown for therapy response, but even with this small number of samples there is an indication that neutrophil defensins expression could also be associated with histological type and stage of NSCLC-patients.

We have access to additional tissue biopsy samples of the Antwerp University Hospital, to enlarge the current sample set, in order to confirm these additional associations of neutrophil defensins with clinicopathological characteristics. In addition and through the University Hospital of Antwerp we have access to biopsy samples including melanoma, breast cancer patients, bladder cancer (urothelial carcinoma) and head and neck squamous cell carcinoma tissues, allow us to extend the present study to additional cancer types, also treatable with anti-PD-(L)1 immunotherapy, wherein the neutrophil defensins are at least expected to act as predictive biomarkers for therapy response.

TABLE 5

Association of neutrophil defensin expression with clinicopathological characteristics.

| | Neutrophil Defensin Expression on Tumor Cells | | | Neutrophil Defensin Expression on Immune Cells | | |
|---|---|---|---|---|---|---|
| | Low(<2%) | High (≥2%) | p-Value | Low(<2%) | High (≥2%) | p-Value |
| **Gender** | | | | | | |
| Female | 8 (47.1%) | 3 (37.5%) | 1 | 9 (56.3%) | 2 (22.2%) | 0.21 |
| Male | 9 (52.9%) | 5 (62.5%) | | 7 (43.7%) | 7 (77.8%) | |
| **Histologic type** | | | | | | |
| Adenocarcinoma | 13 (76.5%) | 4 (50%) | 0.22 | 12 (75%) | 5 (55.6%) | 0.33 |
| Squamous | 4 (23.5%) | 3 (37.5%) | | 3 (18.7%) | 4 (44.4%) | |
| Large cell | | 1 (12.5%) | | 1 (6.3%) | | |
| **Stage** | | | | | | |
| IIb | 1 (5.9%) | | 0.15 | | 1 (11.1%) | 0.09 |
| IIIa | | 2 (25%) | | | 2 (22.2%) | |
| IVa | 11 (64.7%) | 5 (62.5%) | | 11 (68.8%) | 5 (55.6%) | |
| IVb | 5 (29.4%) | 1 (12.5%) | | 5 (31.2%) | 1 (11.1%) | |
| **Smoking Status** | | | | | | |
| Never-smoker | 2 (11.8%) | 1 (12.5%) | 1 | 1 (6.25%) | 2 (22.2%) | 0.53 |
| Smoker | 14 (82.3%) | 7 (87.5%) | | 14 (87.5%) | 7 (77.8%) | |
| Unknown | 1 (5.9%) | | | 1 (6.25%) | | |
| **Therapy Response** | | | | | | |
| Responder | 3 (17.6%) | 6 (75%) | | 3 (18.7%) | 6 (66.7%) | |
| Non-responder | 14 (82.4%) | 2 (25%) | | 13 (81.3%) | 3 (33.3%) | |

REFERENCES

1. International Agency for Research on Cancer. Globocan. Http://Gco.Iarc.Fr/Today. Http://Gco.Iarc.Fr/Today 2018, 876, 2018-2019.
2. Garon, E. B.; Rizvi, N. A.; Hui, R.; Leighl, N.; Balmanoukian, A. S.; Eder, J. P.; Patnaik, A.; Aggarwal, C.; Gubens, M.; Horn, L.; Carcereny, E.; Ahn, M.-J.; Felip, E.; Lee, J.-S.; Hellmann, M. D.; Hamid, O.; Goldman, J. W.; Soria, J.-C.; Dolled-Filhart, M.; Rutledge, R. Z.; Zhang, J.; Lunceford, J. K.; Rangwala, R.; Lubiniecki, G. M.; Roach, C.; Emancipator, K. & Gandhi, L. Pembrolizumab for the Treatment of Non-Small-Cell Lung Cancer. N. Engl. J. Med. 2015, 372, 2018-2028.
3. Zappa, C. & Mousa, S. A. Non-small cell lung cancer: current treatment and future advances. Transl. Lung Cancer Res. 2016, 5, 288-300.
4. Singh, P. K.; Singh, H. & Silakari, O. Kinases inhibitors in lung cancer: From benchside to bedside. Biochim. Biophys. Acta-Rev. Cancer 2016, 1866, 128-140.
5. Pardoll, D. M. The blockade of immune checkpoints in cancer immunotherapy. Nat. Rev. Cancer 2012, 12, 252-264.
6. Johnson, D. B.; Peng, C. & Sosman, J. A. Nivolumab in melanoma: Latest evidence and clinical potential. Ther. Adv. Med. Oncol. 2015, 7, 97-106.
7. Teixidó, C.; Vilariño, N.; Reyes, R. & Reguart, N. PD-L1 expression testing in non-small cell lung cancer. Ther. Adv. Med. Oncol. 2018, 10, 1-17.
8. Riley, J. L. PD-1 signaling in primary T cells. Immunol Rev. 2009, 229, 114-125.
9. Mellman, I.; Coukos, G. & Dranoff, G. Cancer immunotherapy comes of age. Nature 2014, 480, 480-489.
10. Pembrolizumab . . . .
11. Nivolumab . . . .
12. Davies, M. New modalities of cancer treatment for NSCLC: Focus on immunotherapy. Cancer Manag. Res. 2014, 6, 63-75.
13. Atezolizumab . . . .
14. Blair, H. A. Atezolizumab: A Review in Previously Treated Advanced Non-Small Cell Lung Cancer. Target. Oncol. 2018, 13, 399-407.
15. Tray, N.; Weber, J. S. & Adams, S. Predictive Biomarkers for Checkpoint Immunotherapy: Current Status and Challenges for Clinical Application. Cancer Immunol. Res. 2018, 6, 1122-1128.
16. Vilain, R. E.; Menzies, A. M.; Wilmott, J. S.; Kakavand, H.; Madore, J.; Guminski, A.; Liniker, E.; Kong, B. Y.; Cooper, A. J.; Howle, J. R.; Saw, R. P. M.; Jakrot, V.; Lo, S.; Thompson, J. F.; Carlino, M. S.; Kefford, R. F.; Long, G. V. & Scolyer, R. A. Dynamic changes in PD-L1 expression and immune infiltrates early during treatment predict response to PD-1 blockade in Melanoma. Clin. Cancer Res. 2017, 23, 5024-5033.
17. Khunger, M.; Hernandez, A. V.; Pasupuleti, V.; Rakshit, S.; Pennell, N. A.; Stevenson, J.; Mukhopadhyay, S.; Schalper, K. & Velcheti, V. Programmed Cell Death 1 (PD-1) Ligand (PD-L1) Expression in Solid Tumors As a Predictive Biomarker of Benefit From PD-1/PD-L1 Axis Inhibitors: A Systematic Review and Meta-Analysis. JCO Precis. Oncol. 2017, 1, 1-15.
18. Velcheti, V.; Schalper, K. A.; Carvajal, D. E.; Rimm, D. L.; Anagnostou, V. K.; Syrigos, K. N.; Sznol, M.; Herbst, R. S.; Gettinger, S. N. & Chen, L. Programmed death ligand-1 expression in non-small cell lung cancer. Lab Invest 2014, 94, 107-116.
19. Robert, C.; Long, G. V; Brady, B.; Dutriaux, C.; Maio, M.; Mortier, L.; Hassel, J. C.; Rutkowski, P.; McNeil, C.; Kalinka-Warzocha, E.; Savage, K. J.; Hernberg, M. M.; Lebbé, C.; Charles, J.; Mihalcioiu, C.; Chiarion-Sileni, V.; Mauch, C.; Cognetti, F.; Arance, A.; Schmidt, H.;

Schadendorf, D.; Gogas, H.; Lundgren-Eriksson, L.; Horak, C.; Sharkey, B.; Waxman, I. M.; Atkinson, V. & Ascierto, P. A. Nivolumab in previously untreated melanoma without BRAF mutation. N. Engl. J. Med. 2015, 372, 320-330.

20. Daud, A. I.; Wolchok, J. D.; Robert, C.; Hwu, W. J.; Weber, J. S.; Ribas, A.; Hodi, F. S.; Joshua, A. M.; Kefford, R.; Hersey, P.; Joseph, R.; Gangadhar, T. C.; Dronca, R.; Patnaik, A.; Zarour, H.; Roach, C.; Toland, G.; Lunceford, J. K.; Li, X. N.; Emancipator, K.; Dolled-Filhart, M.; Kang, S. P.; Ebbinghaus, S. & Hamid, O. Programmed death-ligand 1 expression and response to the anti-programmed death 1 antibody pembrolizumab in melanoma. J. Clin. Oncol. 2016, 34, 4102-4109.

21. Taube, J. M.; Klein, A.; Brahmer, J. R.; Xu, H.; Pan, X.; Kim, J. H.; Chen, L.; Pardoll, D. M.; Topalian, S. L. & Anders, R. A. Association of PD-1, PD-1 ligands, and other features of the tumor immune microenvironment with response to anti-PD-1 therapy. Clin Cancer Res 2015, 20, 5064-5074.

22. Jacobs, J.; Zwaenepoel, K.; Rolfo, C.; Bossche, J. Van den; Deben, C.; Silence, K.; Hermans, C.; Smits, E.; Van Schil, P.; Lardon, F.; Deschoolmeester, V. & Pauwels, P. Unlocking the potential of CD70 as a novel immunotherapeutic target for non-small cell lung cancer. Oncotarget 2015, 6, 13462-13475.

23. Teixidó, C.; Karachaliou, N.; Gonzalez-Cao, M.; Morales-Espinosa, D. & Rosell, R. Assays for predicting and monitoring responses to lung cancer immunotherapy. Cancer Biol. Med. 2015, 12, 87-95.

24. Berghmans, E.; Van Raemdonck, G.; Schildermans, K.; Willems, H.; Boonen, K.; Maes, E.; Mertens, I.; Pauwels, P. & Baggerman, G. MALDI Mass Spectrometry Imaging Linked with Top-Down Proteomics as a Tool to Study the Non-Small-Cell Lung Cancer Tumor Microenvironment. Methods Protoc. 2019, 2, 1-21.

25. Chughtai, K. & Heeren, R. M. A. Mass Spectrometric Imaging for Biomedical Tissue Analysis-Chemical Reviews (ACS Publications). Chem. Rev. 2011, 110, 3237-3277.

26. Ahlf Wheatcraft, D. R.; Liu, X. & Hummon, A. B. Sample Preparation Strategies for Mass Spectrometry Imaging of 3D Cell Culture Models. J. Vis. Exp. 2014, 1-7.

27. Minerva, L.; Clerens, S.; Baggerman, G. & Arckens, L. Direct profiling and identification of peptide expression differences in the pancreas of control and ob/ob mice by imaging mass spectrometry. Proteomics 2008, 8, 3763-3774.

28. Stoeckli, M.; Chaurand, P.; Hallahan, D. E. & Caprioli, R. M. Imaging mass spectrometry: A new technology for the analysis of protein expression in mammalian tissues. Nat. Med. 2001, 7, 493-496.

29. Minerva, L.; Boonen, K.; Menschaert, G.; Landuyt, B.; Baggerman, G. & Arckens, L. Linking Mass Spectrometric Imaging and Traditional Peptidomics: A validation in the Obese Mouse Model. Anal. Chem. 2011, 83, 7682-7691.

30. Zhang, L. & Gallo, R. L. Antimicrobial peptides. Curr. Biol. 2016, 26, 14-19.

31. Plichta, J. K.; Nienhouse, V. & Radek, K. A. Integrating "omics" technologies to conceptualize dynamic antimicrobial peptide responses. Front. Immunol. 2012, 3, 1-4.

32. Ganz, T. The Role of Antimicrobial Peptides in Innate Immunity. Integr. Comp. Biol. 2003, 43, 300-304.

33. Mukae, H.; Iiboshi, H.; Nakazato, M.; Hiratsuka, T.; Tokojima, M.; Abe, K.; Ashitani, J.; Kadota, J.; Matsukura, S. & Kohno, S. Raised plasma concentrations of α-defensins in patients with idiopathic pulmonary fibrosis. Thorax 2002, 57, 623-628.

34. Stenzinger, A.; Schwamborn, K.; Kazdal, D.; Fresnais, M.; Schirmacher, P.; Casadonte, R.; Leichsenring, J.; Kriegsmann, M.; Kriegsmann, K.; Zgorzelski, C.; Weichert, W.; Hundemer, M.; Kriegsmann, J.; Harms, A.; Warth, A. & Longuespée, R. Combined Immunohistochemistry after Mass Spectrometry Imaging for Superior Spatial Information. PROTEOMICS—Clin. Appl. 2018, 13, 1800035.

35. Biobank . . . .

36. Bemis, K. D.; Harry, A.; Eberlin, L. S.; Ferreira, C.; Van De Ven, S. M.; Mallick, P.; Stolowitz, M. & Vitek, O. Cardinal: An R package for statistical analysis of mass spectrometry-based imaging experiments. Bioinformatics 2015, 31, 2418-2420.

37. Fellers, R. T.; Greer, J. B.; Early, B. P.; Yu, X.; LeDuc, R. D.; Kelleher, N. L. & Thomas, P. M. ProSight Lite: Graphical Software to Analyze Top-Down Mass Spectrometry Data. Proteomics 2015, 15, 1235-1238.

38. Casadonte, R. & Caprioli, R. M. Proteomic analysis of formalin-fixed paraffin embedded tissue by MALDI imaging mass spectrometry. Nat. Protoc. 2012, 6, 1695-1709.

39. Ly, A.; Buck, A.; Balluff, B.; Sun, N.; Gorzolka, K.; Feuchtinger, A.; Janssen, K. P.; Kuppen, P. J. K.; Van De Velde, C. J. H.; Weirich, G.; Erlmeier, F.; Langer, R.; Aubele, M.; Zitzelsberger, H.; McDonnell, L.; Aichler, M. & Walch, A. High-mass-resolution MALDI mass spectrometry imaging of metabolites from formalin-fixed paraffin-embedded tissue. Nat. Protoc. 2016, 11, 1428-1443.

40. Cole, S. R.; Ma, X.; Zhang, X. & Xia, Y. Electron Transfer Dissociation (ETD) of peptides containing intrachain disulfide bonds. J. Am. Soc. Mass Spectrom. 2012, 23, 310-320.

41. Shiaw-Lin Wu, Haitao Jiang, Qiaozhen Lu, Shujia Dai, William S. Hancock, and B. L. K. Mass Spectrometric Determination of Disulfide Linkages in Recombinant Therapeutic Proteins Using On-line LC-MS with Electron Transfer Dissociation (ETD). Anal. Chem. 2009, 81, 112-122.

42. Compton, P. D.; Strukl, J. V.; Bai, D. L.; Shabanowitz, J. & Hunt, D. F. Optimization of electron transfer dissociation via informed selection of reagents and operating parameters. Anal. Chem. 2012, 84, 1781-1785.

43. Gaspar, D.; Freire, J. M.; Pacheco, T. R.; Barata, J. T. & Castanho, M. A. R. B. Apoptotic human neutrophil peptide-1 anti-tumor activity revealed by cellular biomechanics. Biochim. Biophys. Acta-Mol. Cell Res. 2015, 1853, 308-316.

44. Xu, N.; Wang, Y.-s.; Pan, W.-b.; Xiao, B.; Wen, Y.-j.; Chen, X.-c.; Chen, L.-j.; Deng, H.-x.; You, J.; Kan, B.; Fu, A.; Li, D.; Zhao, X. & Wei, Y.-q. Human-defensin-1 inhibits growth of human lung adenocarcinoma xenograft in nude mice. Mol. Cancer Ther. 2008, 7, 1588-1597.

45. Bateman, A.; Singh, A.; Jothy, S.; Fraser, R.; Esch, F. & Solomon, S. The levels and biologic action of the human neutrophil granule peptide HP-1 in lung tumors. Peptides 1992, 13, 133-139.

46. Müller, C. A.; Markovic-Lipkovski, J.; Klatt, T.; Gamper, J.; Schwarz, G.; Beck, H.; Deeg, M.; Kalbacher, H.; Widmann, S.; Wessels, J. T.; Becker, V.; Müller, G. A. & Flad, T. Human α-Defensins HNPs-1, -2, and -3 in Renal Cell Carcinoma. Am. J. Pathol. 2002, 160, 1311-1324.

47. Bauer, J. A.; Chakravarthy, A. B.; Rosenbluth, J. M.; Mi, D.; Seeley, E. H.; Granja-Ingram, N. D. M.; Olivares, M. G.; Kelley, M. C.; Mayer, I. A.; Meszoely, I. M.; Means-Powell, J. A.; Johnson, K. N.; Tsai, C. J.; Ayers, G. D.; Sanders, M. E.; Schneider, R. J.; Formenti, S. C.; Caprioli, R. M. & Pietenpol, J. A. Identification of markers of taxane sensitivity using proteomic and genomic analyses of breast tumors from patients receiving neoadjuvant paclitaxel and radiation. Clin. Cancer Res. 2010, 16, 681-690.

48. Ye, Z.; Dong, H.; Li, Y.; Ma, T.; Huang, H.; Leong, H.-S.; Eckel-Passow, J.; Kocher, J.-P. A.; Liang, H.; Wang, L. & Professor, A. Prevalent Homozygous Deletions of Type I Interferon and Defensin Genes in Human Cancers Associate with Immunotherapy Resistance. Clin. Cancer Res. 2018.

49. Metz, B.; Kersten, G. F. A.; Baart, G. J. E.; De Jong, A.; Meiring, H.; Ten Hove, J.; Van Steenbergen, M. J.; Hennink, W. E.; Crommelin, D. J. A. & Jiskoot, W. Identification of formaldehyde-induced modifications in proteins: Reactions with insulin. Bioconjug. Chem. 2006, 17, 815-822.

50. Rahimi, F.; Shepherd, C. E.; Halliday, G. M.; Geczy, C. L. & Raftery, M. J. Antigen-epitope retrieval to facilitate proteomic analysis of formalin-fixed archival brain tissue. Anal. Chem. 2006, 78, 7216-7221.

51. Foll, M. C.; Fahrner, M.; Oria, V. O.; Kühs, M.; Biniossek, M. L.; Werner, M.; Bronsert, P. & Schilling, O. Reproducible proteomics sample preparation for single FFPE tissue slices using acid-labile surfactant and direct trypsinization. Clin. Proteomics 2018, 15, 1

The invention claimed is:

1. A method of treating a subject with non-small cell lung cancer, the method comprising:

determining whether a cancer sample from the subject comprises one or more antimicrobial peptides selected from the group consisting of neutrophil defensin 1, neutrophil defensin 2 and neutrophil defensin 3; and administering to the subject an effective amount of a PD-1/PD-L1 antagonist when one or more of the antimicrobial peptides are present within the cancer sample.

2. The method of claim 1, wherein the PD-1/PD-L1 antagonist is selected from the group consisting of Pembrolizumab, Nivolumab and/or Atezolizumab.

3. The method of claim 1, wherein determining whether the cancer sample comprises one or more antimicrobial peptides comprises analyzing the cancer sample using MALDI-MSI.

4. The method of claim 1, wherein determining whether the cancer sample comprises one or more antimicrobial peptides comprises analyzing the cancer sample using immunohistochemistry.

5. The method of claim 4, wherein analyzing the cancer sample using immunohistochemistry comprises using one or more biomarker-specific antibodies.

6. The method of claim 5, wherein the one or more biomarker-specific antibodies is selected from the group consisting of antibodies against neutrophil defensin 1, antibodies against neutrophil defensin 2 and antibodies against neutrophil defensin 3.

7. The method of claim 1, wherein the cancer sample is a tissue biopsy section.

8. The method of claim 7, wherein the tissue biopsy section comprises formalin-fixed paraffin-embedded tissue biopsy sections.

9. The method of claim 7, wherein the tissue biopsy section comprises fresh frozen tissue biopsy sections.

10. A method of diagnosing and treating a subject with a non-small cell lung cancer likely to respond to an immunotherapy, the method comprising:

obtaining a cancer sample from the subject;

detecting whether one or more antimicrobial peptides selected from the group consisting of neutrophil defensin 1, neutrophil defensin 2, and neutrophil defensin 3 is present in the sample by immunohistochemistry or MALDI-MSI;

diagnosing the subject with a cancer likely to respond to the immunotherapy comprising a PD-1/PD-L1 antagonist when the presence of one or more antimicrobial peptides is detected; and administering an effective amount of the immunotherapy comprising the PD-1/PD-L1 antagonist to the diagnosed subject.

11. The method of claim 10, further comprising detecting whether neutrophil defensin 1, neutrophil defensin 2, and neutrophil defensin 3 are present in the cancer sample.

12. The method of claim 10, wherein the PD-1/PD-L1 antagonist is selected from the group consisting of Pembrolizumab, Nivolumab and/or Atezolizumab.

* * * * *

```
                          SEQUENCE LISTING


<160> NUMBER OF SEQ ID NOS: 3

<210> SEQ ID NO 1
<211> LENGTH: 30
<212> TYPE: PRT
<213> ORGANISM: Homo sapiens

<400> SEQUENCE: 1

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30


<210> SEQ ID NO 2
<211> LENGTH: 29
<212> TYPE: PRT
<213> ORGANISM: Homo sapiens

<400> SEQUENCE: 2

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25


<210> SEQ ID NO 3
<211> LENGTH: 30
<212> TYPE: PRT
<213> ORGANISM: Homo sapiens

<400> SEQUENCE: 3

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30
```